(12) United States Patent
Tsupryk et al.

(10) Patent No.: US 8,582,098 B2
(45) Date of Patent: Nov. 12, 2013

(54) SINGLE PHOTON SPECTROMETER

(75) Inventors: Andriy Tsupryk, Coram, NY (US); Ivan Tovkach, Centereach, NY (US); Dmitriy Gavrilov, Setauket, NY (US); Georgiy Gudkov, Coram, NY (US); Tetyana Gudkova, legal representative, Coram, NY (US); Vera Gorfinkel, Brook, NY (US); Boris Gorbovitski, Stony Brook, NY (US); Dmytro Gudkov, Stony Brook, NY (US)

(73) Assignee: The Research Foundation of State University of New York, Albany, NY (US)

( * ) Notice: Subject to any disclaimer, the term of this patent is extended or adjusted under 35 U.S.C. 154(b) by 473 days.

(21) Appl. No.: 12/734,365

(22) PCT Filed: Oct. 24, 2008

(86) PCT No.: PCT/US2008/012087
§ 371 (c)(1),
(2), (4) Date: Nov. 19, 2010

(87) PCT Pub. No.: WO2009/055012
PCT Pub. Date: Apr. 30, 2009

(65) Prior Publication Data
US 2011/0108711 A1     May 12, 2011

Related U.S. Application Data

(60) Provisional application No. 61/000,320, filed on Oct. 25, 2007.

(51) Int. Cl.
*G01J 3/42* (2006.01)
*G01J 1/42* (2006.01)

(52) U.S. Cl.
USPC .......................... 356/317; 356/320; 356/222

(58) Field of Classification Search
USPC .................................. 356/300–334, 402–425
See application file for complete search history.

(56) References Cited

U.S. PATENT DOCUMENTS

| 4,784,486 A | * | 11/1988 | Van Wagenen et al. | ...... 356/301 |
| 5,323,010 A | * | 6/1994 | Gratton et al. | ............. 250/458.1 |

(Continued)

FOREIGN PATENT DOCUMENTS

WO     WO03004982     1/2003

OTHER PUBLICATIONS

International Search Report issued by the International Searching Authority (ISA/US) on Jun. 23, 2009 in connection with International Application No. PCT/US2008/012087.

(Continued)

*Primary Examiner* — Gregory J Toatley
*Assistant Examiner* — Maurice Smith
(74) *Attorney, Agent, or Firm* — John P. White; Cooper & Dunham LLP

(57) ABSTRACT

A fiberized single photon sensitive spectrometer based on a 32-channel PMT sensor is highly sensitive with broad detection dynamic range. The spectrometer enables accurate and high speed detection, identification and analysis of biological samples labeled with multiple fluorescent markers, such as compositions of multi-color fluorescence signals or radiation emitted by multiple fluorescence dyes. A fiberized optical input of the spectrometer allows an easy and efficient coupling to any measurement system based on fiber collection of the analyzed fluorescence. The spectrometer provides highly accurate DNA sequencing. A 32 channel PMT single photon detector has a detection dynamic range of more than 20 bits and has a frame rate of about 3300 frames per second. The dynamic range of the detector's pixels reaches $10^8$ photocounts per second.

16 Claims, 26 Drawing Sheets

(56) References Cited

U.S. PATENT DOCUMENTS 5,774,520 A * 6/1998 Bolotin ........................ 378/50
6,320,196 B1 * 11/2001 Dorsel et al. ............... 250/458.1
6,463,314 B1 * 10/2002 Haruna ........................ 600/407
7,403,286 B2 7/2008 Kato

OTHER PUBLICATIONS

Written Opinion of the International Searching Authority issued by the International Searching Authority (ISA/US) on Jun. 23, 2009 in connection with International Application No. PCT/US2008/012087.
International Preliminary Report on Patentability issued by the International Bureau of WIPO on Apr. 27, 2010 in connection with International Application No. PCT/US2008/012087.
Pakhlov, P. (Dec. 14, 2005). *SiPM: Development and Applications* [PowerPoint slides] . Retrieved from http://rd.kek.jp/slides/20051214/SiPM.ppt.

* cited by examiner

| Excitation | Ar-ion laser (488 & 514nm, 18mW) | | | |
|---|---|---|---|---|
| Base | Color deconvolution matrix | | | |
| G | 1 | 0.842 | 0.297 | 0.124 |
| A | 0.147 | 1 | 0.366 | 0.264 |
| T | 0.007 | 0.104 | 1 | 0.809 |
| C | 0 | 0.008 | 0.057 | 1 |

$C_{Ar-ion} =$

| Excitation | Nd-YAG laser (532nm, 17mW) | | | |
|---|---|---|---|---|
| Base | Color deconvolution matrix | | | |
| G | 1 | 0.679 | 0.254 | 0.084 |
| A | 0.416 | 1 | 0.285 | 0.179 |
| T | 0.009 | 0.253 | 1 | 0.493 |
| C | 0.025 | 0.024 | 0.109 | 1 |

$C_{Nd-YAG}$

SINGLE PHOTON SPECTROMETER

CLAIM OF PRIORITY

This application is a §371 national stage of PCT International Application No. PCT/US2008/012087, filed Oct. 24, 2008, and claims the benefit of U.S. Provisional Application No. 61/000,320, filed Oct. 24, 2008, the contents of all of which are hereby incorporated by reference into this application.

This invention was made with government support under grant number HG003717 awarded by the National Institute of Health. The government has certain rights in the invention.

FIELD OF THE INVENTION

The present disclosure relates to sensor systems and, in particular, to single photon sensor systems and methods for detecting multi-color fluorescence radiation from, and analysis of, biological samples labeled with multiple fluorescent markers. The sensor systems and detection methods include an optical spectra separation unit, a detection unit and signal processing algorithms for collected data.

BACKGROUND OF THE INVENTION

A number of fluorescence detection techniques are available based on registering single photons. Such techniques are commonly referred to as single photon detection (SPD) techniques. Because of their complexity and cost, in biomedical applications single-photon detection techniques are mostly used for time resolved fluorescence spectroscopy or detection of single fluorescent molecules.

As shown in the block diagram of FIG. 1, the conventional single photon detector heretofore consisted of several modules including a single photon sensor or photo-multiplying tube (PMT) detector, a pulse amplifier, a pulse shaper, a counter, and a computer. A factor impeding the performance of single photon detectors heretofore is the relatively narrow linearity dynamic range of available photon counting devices. A detector's dynamic range is determined by the response time, $\tau_{RESPONSE}$, needed for the detector to respond to a single photon. The quantity $\tau_{RESPONSE}$ depends on the response times of all of the modules of the device and is generally considered to be the sum of response times of the individual modules. As shown in the graph of FIG. 2, in practice the shortest response time in currently available single photon sensors is about 1ns. However, conventional single photon PMT detectors with a given $\tau_{RESPONSE}$, have heretofore been limited to a dynamic range of $10^6$-$10^7$ photocounts per second.

In biological applications, and in particular in DNA detection, DNA sequencing systems have heretofore been unable to process and detect ultra-high speed DNA sequencing. In fact, conventional DNA sequencers have been limited to a recording sequencing process at 10-30 frames per second. Moreover, the dynamic range of conventional DNA machines has been limited to 16 bit. Conventional equipment for serial dilutions of BigDye DNA sequencing standard have heretofore been relatively insensitive by at least a factor of 10 less than what is desirable.

Accordingly, there is a need for sensors including single photon detectors with photon counters having linearity range exceeding $10^7$ photocounts per second, for example up to $10^8$ photocounts per second, DNA sequencing processing capability of greater than 10-30 frames per second and a far more sensitive BigDye DNA sequencing standard. Spectrometers based upon multi-channel single photon detectors, for example based upon a 32-channel PMT sensor, would enable a very accurate, high speed detection of multi-color radiation. In particular, such detectors would demonstrate highly accurate and fast recognition of combinations of fluorescent moieties, and high quality detection of DNA sequencing.

SUMMARY OF THE INVENTION

A fiberized single photon sensitive spectrometer based on a 32-channel PMT sensor is highly sensitive with broad detection dynamic range. The spectrometer enables accurate and high speed detection, identification and analysis of biological samples labeled with multiple fluorescent markers, such as compositions of multi-color fluorescence signals or radiation emitted by multiple fluorescence dyes. A fiberized optical input of the spectrometer allows an easy and efficient coupling to any measurement system based on fiber collection of the analyzed fluorescence. The spectrometer provides highly accurate DNA sequencing. A 32 channel PMT single photon detector has a detection dynamic range of more than 20 bits and has a frame rate of about 3300 frames per second. The dynamic range of the detector's pixels may reach $10^7$ photocounts per second and can be enhanced by a factor of 10.

Signal processing methods are employed which effectively increase the dynamic range of multi-channel detectors to enable detection and recognition of combinations of multiple fluorescent moieties. In one embodiment, a fluorescence detecting sensor is described which is able to measure single photon radiation emitted by mixtures of minute amounts of multiple fluorescence dyes and very accurately determine the content of individual dyes in a dye mixture. Such a sensor, or single photon detector, including a 32 channel PMT, a pulse amplifier, comparator, and counter may have $\tau_{RESPONSE}$ times equal to or smaller than 1ns, for example 0.1 ns or 0.01 ns. Signal processing algorithms are utilized which enable an accurate separation of fluorescence signals emitted by individual fluorescence dyes.

In particular, the embodiments herein disclose:

Optical fibers communicating polychromatic light to a light spectra separator;

At least one multichannel photosensor, each photosensor channel having photosensitive pixels adapted to receive distinct light spectra from said light spectra separator and to produce current pulses in response to single photons of said received light spectra;

A multichannel amplifier, each amplifier channel adapted to receive said current pulses corresponding to light spectra from a corresponding one of said sensor channels of said multichannel photosensor and to amplify said current pulses; and A multichannel photon counter, each counter channel adapted to receive said amplified current pulses from a corresponding one of said amplifier channels of said multichannel amplifier, said multichannel photon counter having an integrator adapted to sum said amplified current pulses in each counter channel over a predetermined time interval.

There is also disclosed a method for identifying DNA sequences comprising the steps of:

Labeling selected DNA fragments with fluorescent dyes;

Inputting said DNA fragments to an optical fiber separation capillary;

Illuminating said labeled DNA fragments in said optical fiber separation capillary with laser light of a predetermined wavelength to produce fluorescence spectra from said DNA fragments;

Illuminating optical fiber with the fluorescence spectra from said DNA fragments, said optical fiber conveying said fluorescence spectra to a light spectra separator, the output from said light spectra separator being incident upon at least one multichannel photosensor, each photosensor channel having photosensitive pixels adapted receive distinct light spectra from said light spectra separator and to produce current pulses in response to single photons of each different wavelength of said distinct light spectra.

There is further disclosed a method for detecting color encoded microparticles comprising the steps of:

Labeling microparticles with fluorescent dyes;

Suspending said labeled microparticles in a buffer fluid;

Passing said buffer fluid with the labeled microparticles through an optical fiber capillary at a predetermined speed;

Illuminating said labeled microparticles in said optical fiber capillary with laser light to produce fluorescence spectra therefrom;

Illuminating optical fiber with the fluorescence spectra from said labeled microparticles, said optical fiber conveying said fluorescence spectra to a light spectra separator, the output from said light spectra separator being incident upon at least one multichannel photosensor, each photosensor channel having photosensitive pixels adapted receive distinct light spectra from said light spectra separator and to produce current pulses in response to single photons of each different wavelength of said distinct light spectra.

BRIEF DESCRIPTION OF THE DRAWINGS

For a further understanding of the present invention, reference may be had to the following drawings in which.

DETAILED DESCRIPTION OF THE PREFERRED EMBODIMENTS

Figure 1:
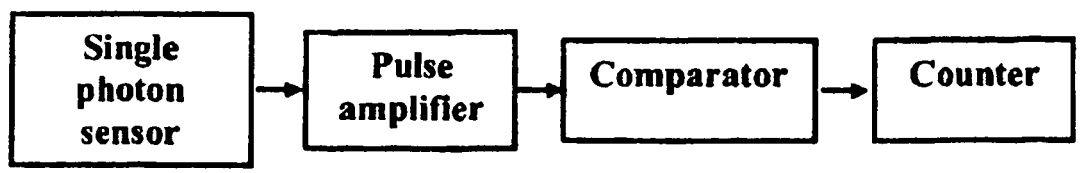
FIG. 1, is a block diagram of a conventional single photon sensor.
Figure 2:
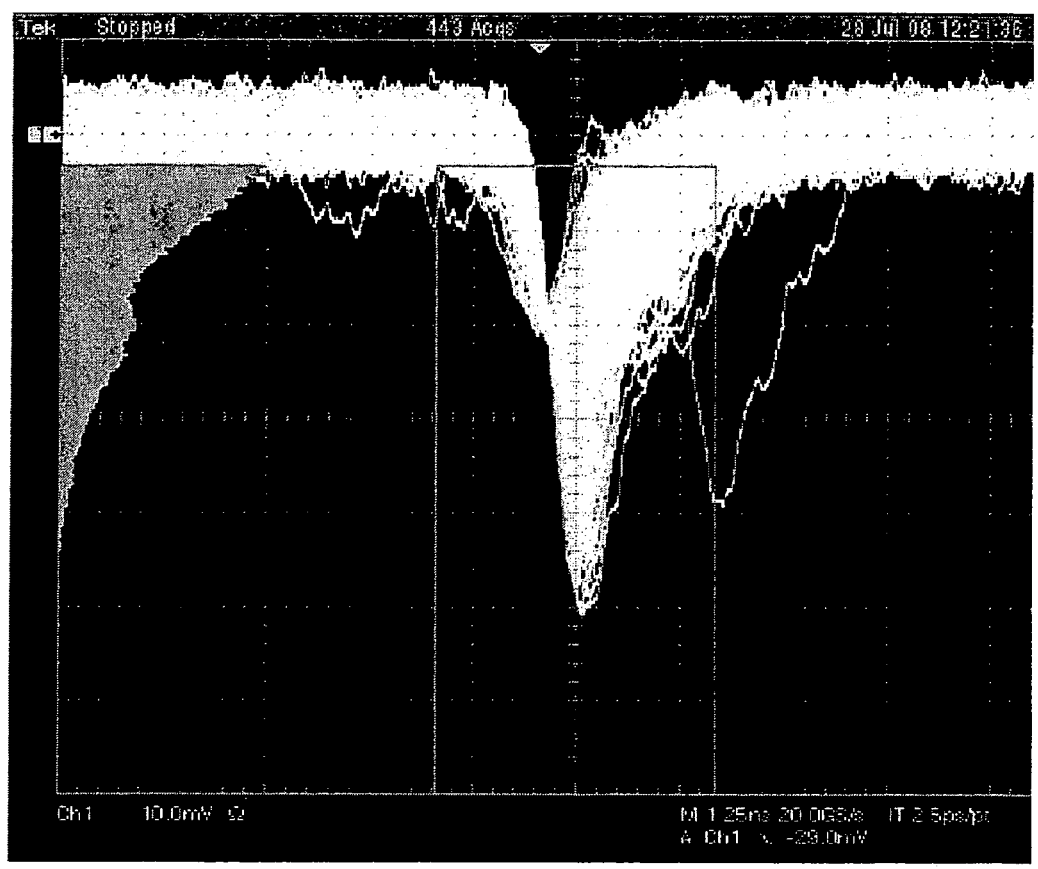
FIG. 2, is a graph showing pulses measured directly from one channel of a commercial 32-channel PMT.
Figure 3:
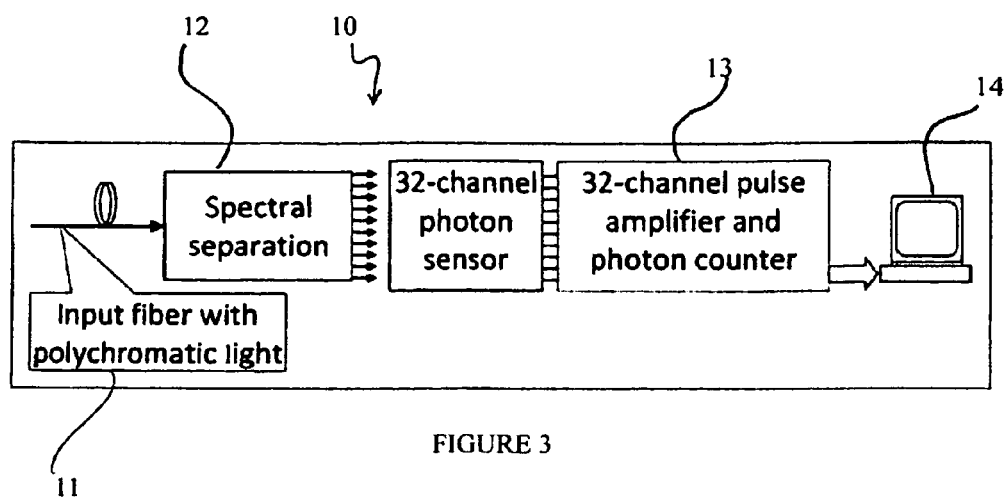
FIG. 3 is a block diagram of a sensor having single photon sensitivity.
Figure 7:
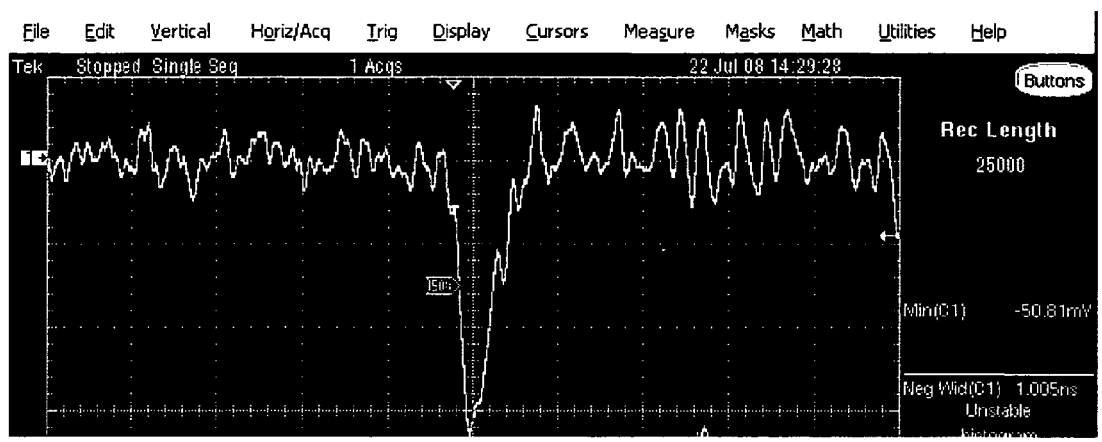
FIG. 7 illustrates a typical 1ns voltage pulse from a PMT.

With reference to FIG. 3, there is shown a block diagram of a sensor 10 having single photon sensitivity for measuring radiation emitted by mixtures of minute amounts of multiple fluorescence dyes. An optical input fiber 11 collects polychromatic fluorescence which is then passed through a spectral separation module 12, schematically illustrated in FIG. 4. After passing through the module 12, the decomposed fluorescent signal illuminates photosensitive pixels of a 32-channel photo-sensor 13, which may be, by way of example only, the 32-channel PMT array H7260-20, which is manufactured by Hamamatsu, Corporation of Japan. Each of the separated wavelengths is detected by one channel of the PMT and each channel of the PMT is capable of detecting wavelengths in the range of about 10 nm. The received photons produce very short current pulses which undergo amplification and photon counting. For example, as shown in FIG. 7, when the PMT is working in a single photon counting mode each channel produces a stream of short, about 1ns, current pulses in response to an incident photon flux. The pulse amplitudes range between 0.4-0.6 mA with corresponding peak voltage between 8 and 12 mV. The pulses are counted by a comparator which is set at a threshold voltage smaller than the pulse amplitude. The obtained photocount is transferred to a computer 14 for recording and data processing.

Figure 4:
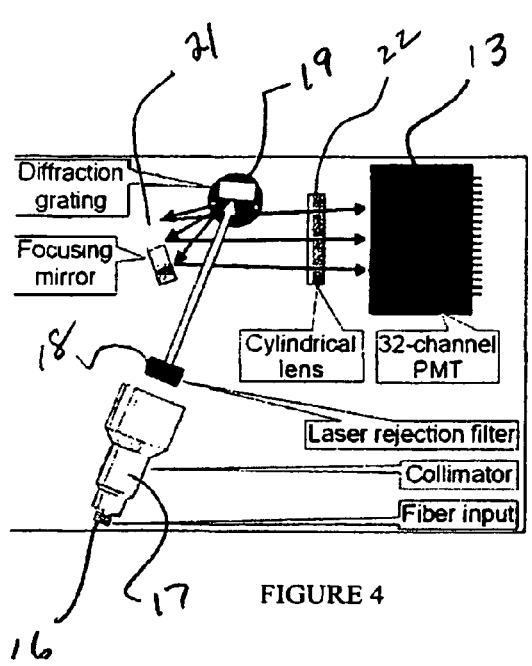
FIG. 4 is a schematic diagram of a spectral separation module.
Figure 4A:
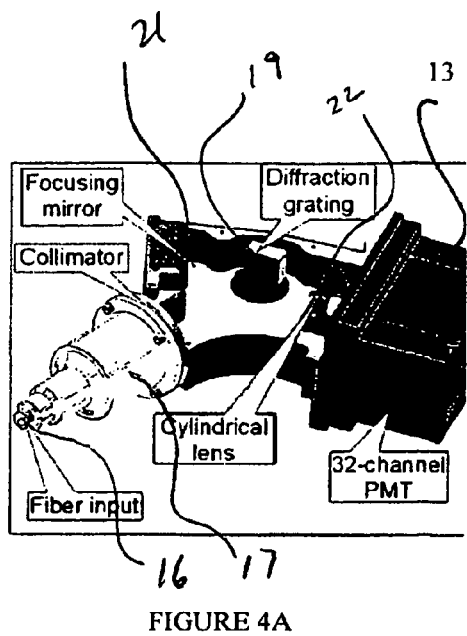
FIG. 4A is a perspective drawing of the spectral separation module of FIG. 4.

In one embodiment, the spectral separation module 12 performs separation and measurement of polychromatic fluorescence within a range of wavelengths from 480 nm to 630 nm. With reference to FIGS. 4 and 4A, the polychromatic fluorescence is presented to the spectral separation module through an optical fiber input 16 coupled to a collimator 17, an example of which may be the F810SMA-543 collimator, manufactured by Thorlabs Inc, NJ. The collimator 17 produces a parallel polychromatic beam of about 10 mm in diameter. The collimated or parallel beam passes through a laser rejection filter 18 and undergoes separation into its constituent wavelength components by a diffraction grating 19, which may be a diffraction grating such as diffraction grating GR13-1850, manufactured by Thorlabs Inc, NJ. In one embodiment, the diffraction grating 19 may be tuned to perform spectral separation and measurement of fluorescence within the range of wavelengths from 490 nm to 630 nm.

The separated monochromatic beam components are focused onto pixels of the 32-channel PMT 13. Such focusing may be accomplished by a spherical focusing mirror 21, which may be the spherical mirror CM254-075-G01, manufactured by Thorlabs Inc, NJ and a cylindrical lens 22, which may be cylindrical lens LJ1095L2, also manufactured by Thorlabs Inc.

In one embodiment, the spectral separation module is capable of detecting wavelengths which differ by 10 nm. Each separate wavelength is mostly detected by one channel of the PMT. Each PMT channel detects wavelengths in the range of about 10 nm.

The spectral separation module of the spectrometer can provide spectral resolution as high as 1 nm. Spectral resolution of about 10 nm may be obtained by a 32-channel PMT having 0.8 mm×7 mm detection zones separated by 0.2 mm distance. It has been found that the overall spectral resolution of the sensor can be improved by using arrays of photoreceiving fibers, each array being connected to illuminate a single photon sensor. The spectral resolution of a spectrometer with a fiber bundle for each photon sensor has been found to be about 5 nm. In fact, the receiving fibers can be used as band pass tillers in some applications when high spectral resolution is required. Where fluorescent dyes have a wide optical spectrum, several arrays of fiber bundles may be used to collect the dye spectrum and to direct it to cover several channels of the spectrometer, as described in more detail below.

Figure 5:
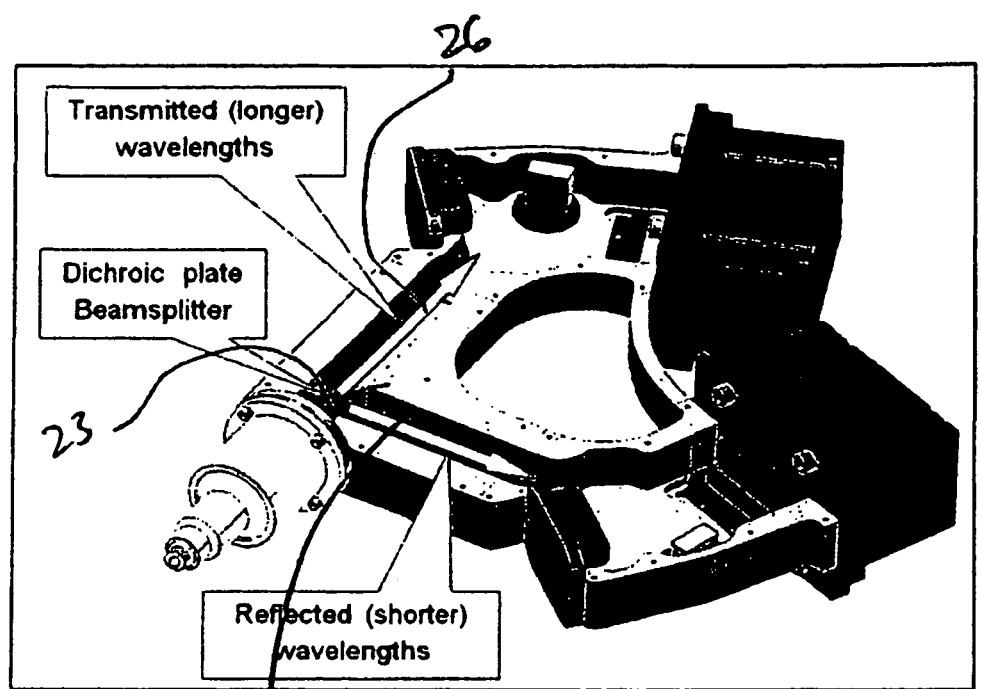
FIG. 5 is a perspective drawing of a double spectral separation module having two 32-channel PMT detectors.

With reference to FIG. 5, one embodiment of a spectrometer may be adapted for a wider range of wavelengths. To increase the range of wavelengths a dichroic plate beam splitter 23 may be used and, as an example only, may be the beam splitter NT47-424, manufactured by Edmund Optics, Inc, NJ. The beam splitter may also be the beam splitter FF650-Di01, manufactured by Semrock Inc., NY. After the incident radiation, or light, is collimated the beam splitter 23 divides the collimated light into two parts. The shorter wavelengths, e.g. 530-585 nm for an Edmund beam splitter or 500-640 nm for a Semrock beam splitter, are deflected into one path 24. At the same time, the longer wavelengths, e.g. 60'-800 nm for an Edmund beam splitter and 660-825 nm for a Semrock beam splitter, are directed into a second path 26. The longer and shorter wavelengths are thereby spatially separated by approximately 90 degrees within the spectrometer. The use of a dichroic plate beam splitter permits a wider range of spectral separation and better spectral resolution in the spectrometer within wavelength ranges of 500-800 nm and 300-500 nm, depending upon the type of detector equipment. Commercially available detector models 117620-20 and H7620-04 have been found useful, respectively, for such wavelength ranges.

Figure 6:
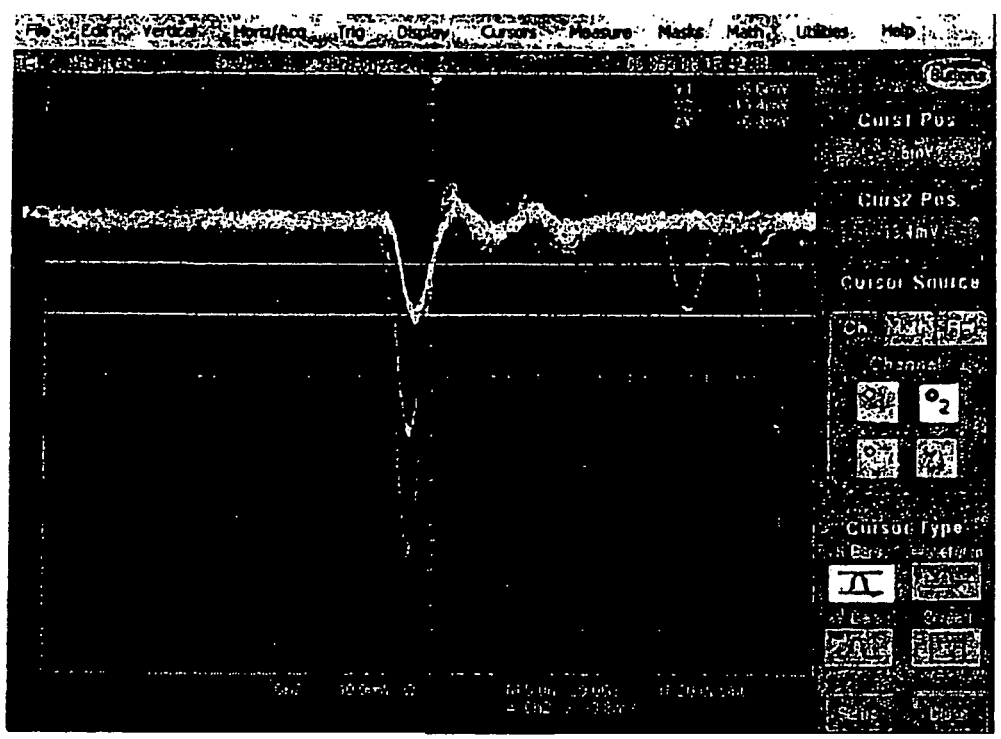
FIG. 6 shows pulses measured from a SiPM diode after amplification with a 400 MHz 26 dB amplifier.
Figure 6A:
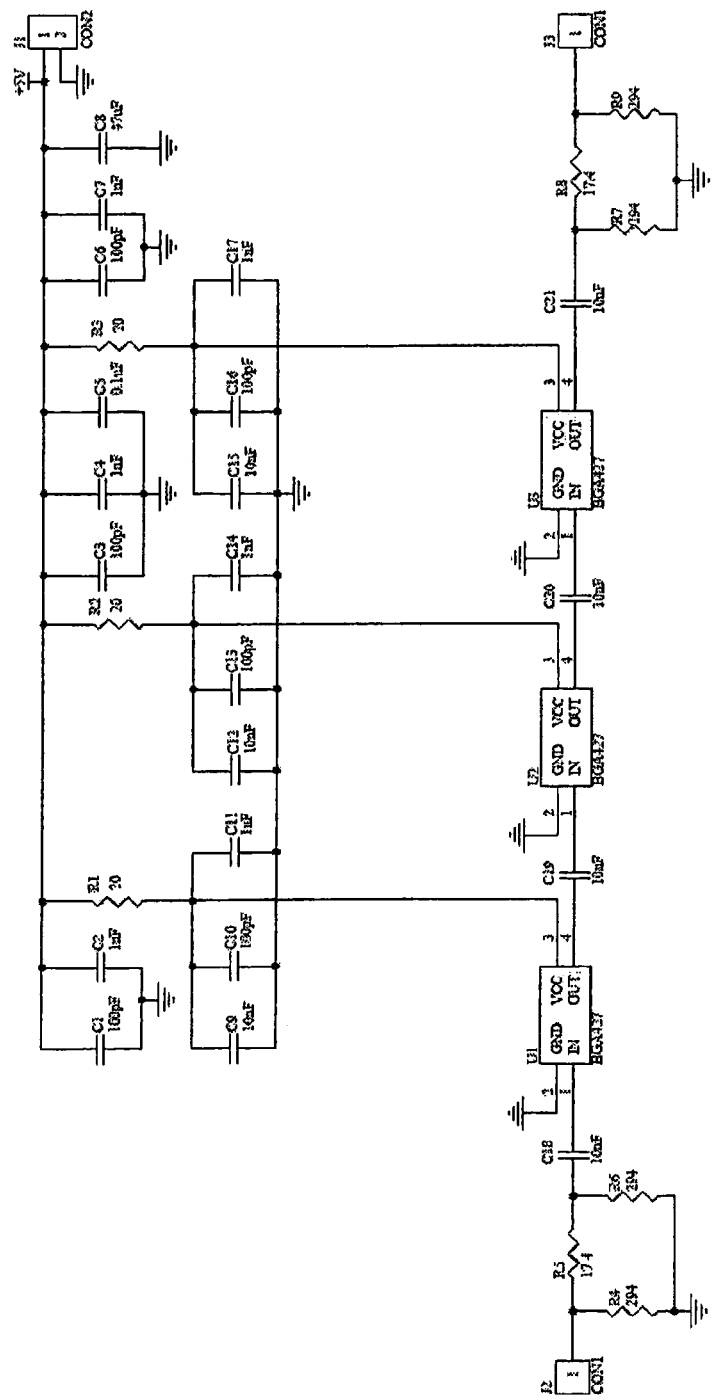
FIG. 6A is an electronic circuit diagram of a 3-stage, 2 GHz, 60 dB pulse amplifier.

Persons of ordinary skill in the relevant art will understand that a sensor or spectrometer may include two different types of multi-channel single photon detectors. For example, without departing from the scope of the invention, a PMT may be used for the longer wavelengths and a silicon photomultiplier, SiPM, diode detector may be used for the shorter wavelengths. The SiPM diode is CMOS technology, relatively inexpensive, and consists of a matrix of individual pixels connected together in parallel on a common silicon substrate. In response to single photons a SiPM produces single voltage pulses. The technology is such that arrays of SiPMs may be used with the driving and read-out electronic circuit integrated on the same chip. SiPMs are high gain, on the order of $10^5$-$10^7$, and operate on relatively low voltage, for example on the order of 20-70V. Their response time varies in the range of 1-20 ns. With reference to FIG. 6, it may be seen that about 2 ns single photon pulses may be obtained from a SiPM diode after amplification with a 400 MHz, 26 dB pulse amplifier. It has been found that 1-stage, 2-stage or 3-stage 2 GHz, 60 dB SiPM pulse amplifiers in conjunction with an SiPM diode can be used as a detector for single photons in single photon counting regime. FIG. 6A shows an electronic circuit diagram for a 3-stage, 2 GHz, 60 dB pulse amplifier. SiPM arrays may also be used as a single photon sensor for a single photon spectrometer. SiPMs have also been found to be adaptable to the detection of DNA sequencing.

It will be understood by those persons of ordinary skill in the relevant art that a semitransparent mirror may be used in place of a dichroic beam splitter. The use of a semitransparent mirror may increase the detection dynamic range since the entire photon flux received by the spectrometer will be detected by two single photon detectors. Similarly, the photon flux may be split into several fluxes each such flux to be detected by a dedicated single photon detector. Such an approach also can be used to increase a dynamic range of the photon detection system.

Figure 8:
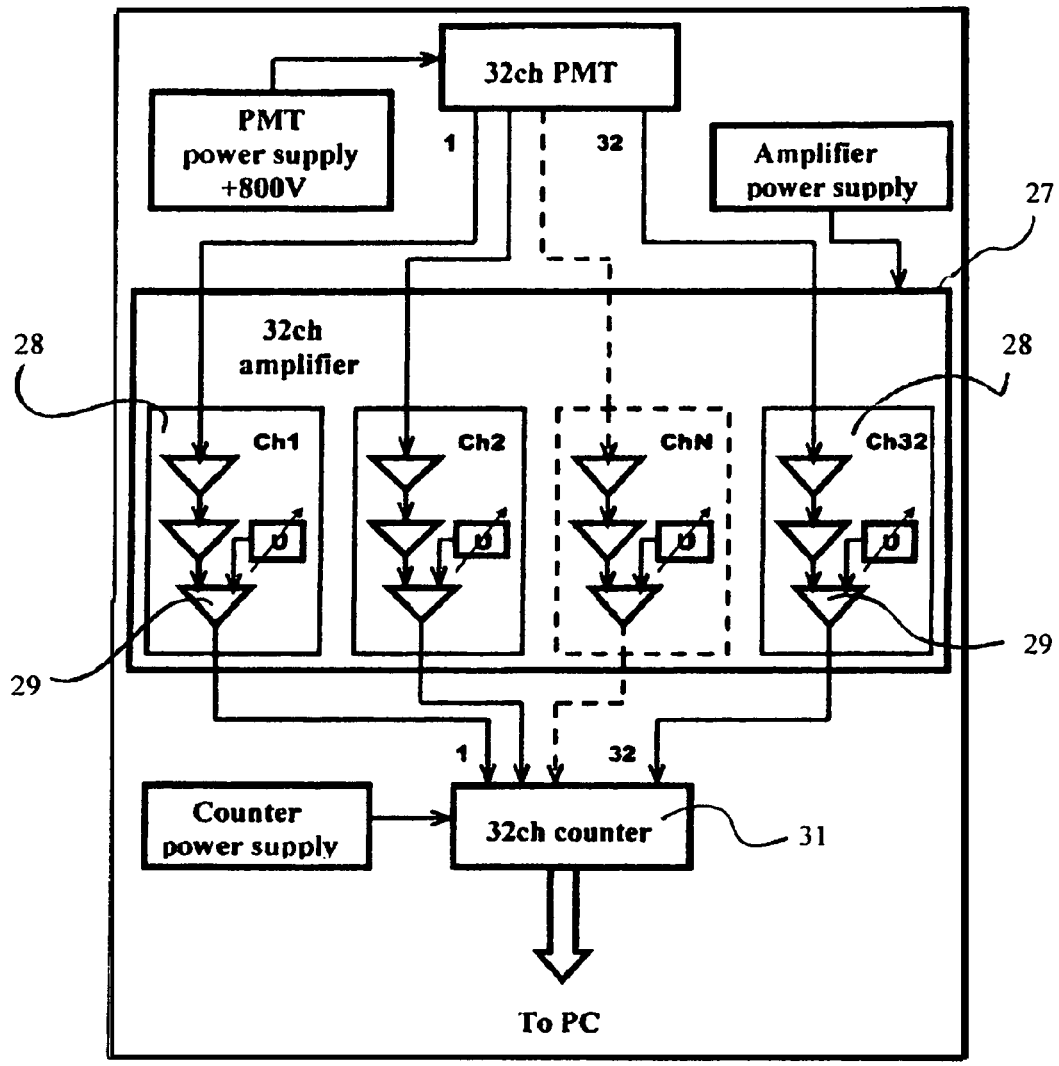
FIG. 8 is a schematic block diagram for a 32 channel single photon detector.
Figure 9:
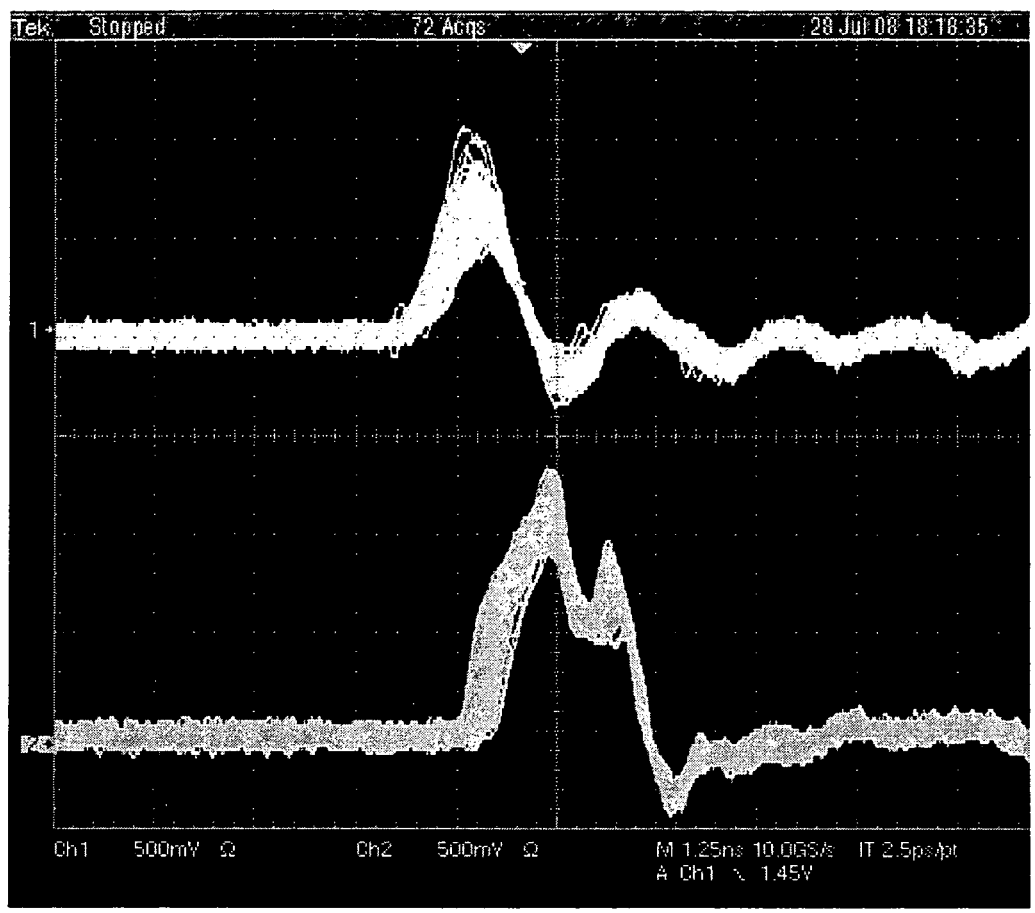
FIG. 9 depicts the pulse shape of amplified pulses from one channel of a 32 channel PMT and pulse shape after a PECL comparator.

With reference to FIG. 8, in one embodiment a detector consists of a 32 channel pulse amplifier 27 that may be based on surface mounted device technology and a 32 channel photon counter 31 that may be based on a field programmed gate array. The amplifier portion of the detector contains 32 identical pulse amplifying channels 28 each of which, in one embodiment, has 35-40 dB gains and 1 GHz bandwidth. The detector may also be provided with 32 fast comparators 29 each having rise and fall times of about 2 ns. This arrangement limits the minimum pulse width to approximately 4.5 ns and increases PMT negative pulses from 10-50 mV to levels that can reliably trigger the comparators. FIG. 9 depicts in the top trace the pulse shape of amplified pulses from one channel of a 32 channel PMT and in the lower trace the pulse shape after a PECL comparator.

Figure 10:
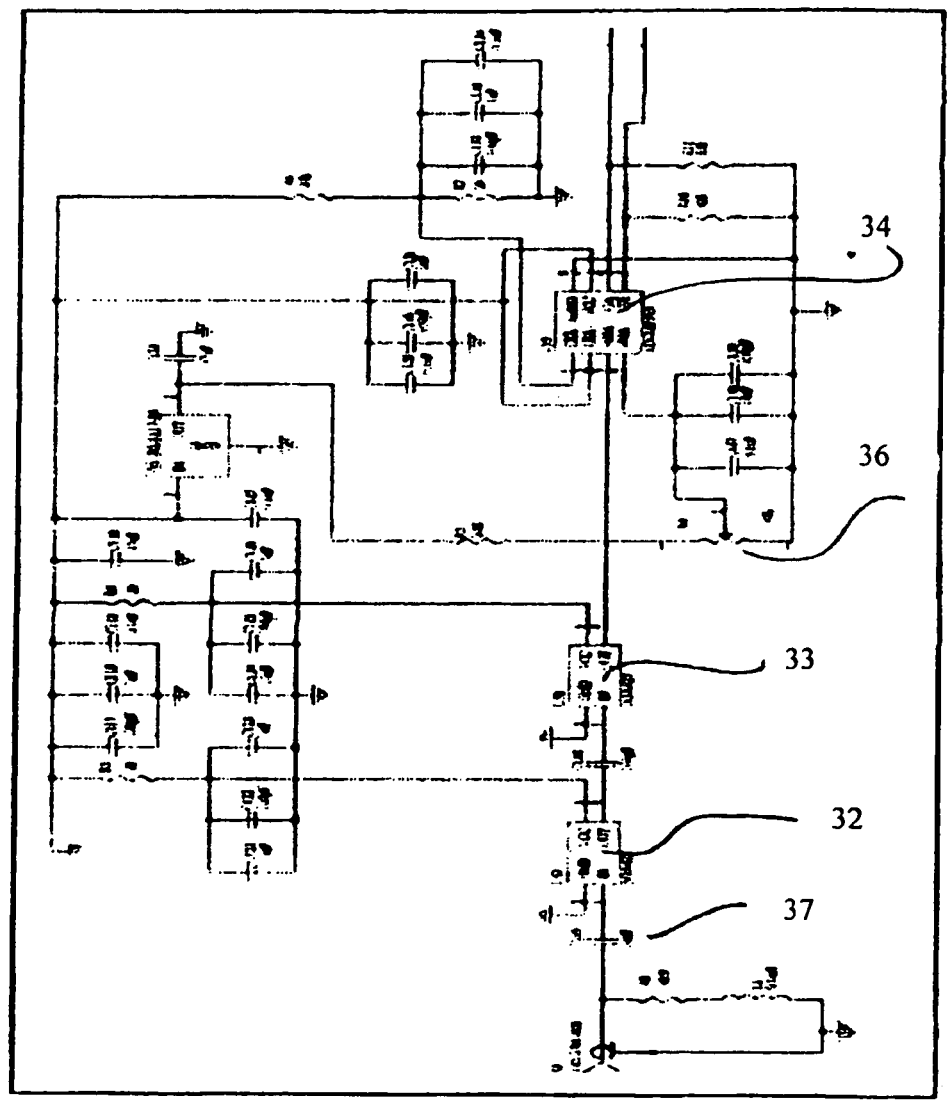
FIG. 10 is a circuit diagram of a 2-stage pulse amplifier.

With reference to FIG. 10, which depicts an embodiment of an electronic circuit for a pulse amplifier, a 2-stage amplifier consists of 2 BGA 427 amplifiers 32 and 33, namely U57 and U58 respectively. Each amplifier stage provides 20 db amplification in the range of 2 GHz. The amplified signal is input to an ADCCMP553 LVPECL comparator 34 having a $\tau_{RESPONSE}$ of Ins. A negative amplified signal pulse generates a PECL-level output pulse from the comparator, which is input to the counter 31 (FIG. 8).

The reference voltage can be adjusted using a potentiometer 36, namely potentiometer R9, from 0 to 3.3 volts. In one embodiment, the reference voltage can be set from 1.2V (the midpoint of the amplifier) up to the amplified pulse height. A threshold voltage can be selected to be as close to the pulse bottom as possible while staying above the noise level. It will be understood that a 1-stage amplifier may also provide sufficient gain for triggering the comparator 34. It such an embodiment, the capacitor 37, namely capacitor C35, may not be used. The resulting circuit provides 20 dB amplification and changes polarity of the pulse only once. As indicated, FIG. 9 depicts in the top trace the pulse shape of amplified pulses before being input to the comparator 34 and in the lower trace the pulse shape of the pulses output from the comparator 34.

Figure 11:
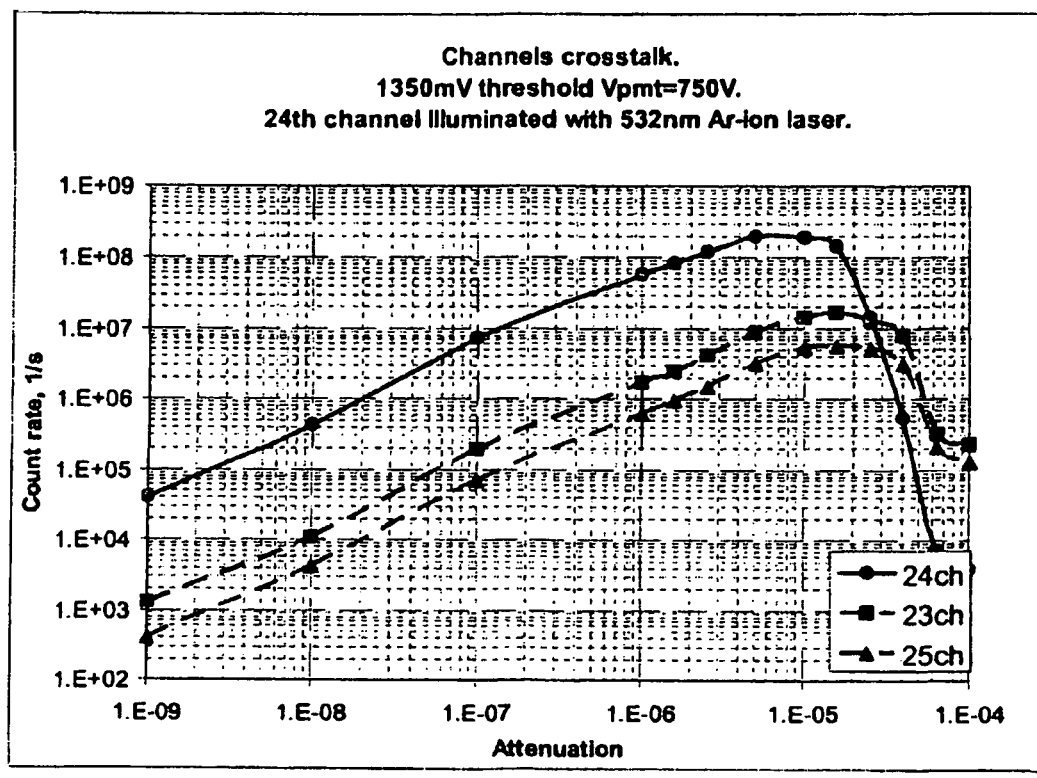
FIG. 11 is a graph showing channel crosstalk of a single photon detector.

Two major types of cross talk may occur in a single photon detector. One type is electronic cross talk inside the 32 channel PMT. FIG. 11 graphically represents typical crosstalk between the neighboring channels of the PMT. Such cross talk arises by certain features of the electronic optics inside of the PMT. The channel cross talk in a 32-channel PMT contains an optical and an electronic component. The optical cross talk arises from illumination of neighboring channels due to imperfect light focusing, and the electronic cross talk is caused by internal electron fluxes between the PMT channels. Minor channel cross talk on the order of 3 percent, may be observed within known 32-channel PMT's when individual channels are illuminated by optical fiber.

The other type of cross talk is electronic cross talk between the amplification channels in the amplifier and the channels in the counter. Generally, electronic cross talk between channels of the amplifier and channels of the 32 channel photon counter has not been observed. However, even very small channel cross talk in the sensor may cause an ambiguity in, for example, the analysis of dye mixtures, particularly when the composition of different dye components differs by orders of magnitude. In order to minimize the optical crosstalk, single PMT channels may be illuminated by focusing on them a beam from a commercial 532 nm NdYAG laser. As can be seen, the entire channel crosstalk is limited to a few percentage points and it is linear relative to the signal measured in the main channel.

Referring again to FIG. 8, after amplification the output from each of the channels of the amplifier 27 is input to the 32 channel high speed photon counter 31. The counter 31 sums the pulses arriving at the channel inputs. The integration time intervals are provided by a synchro-generator in the counter 31 (not shown). In one embodiment, the minimum integration time is about 0.3 ms.

Figure 12:
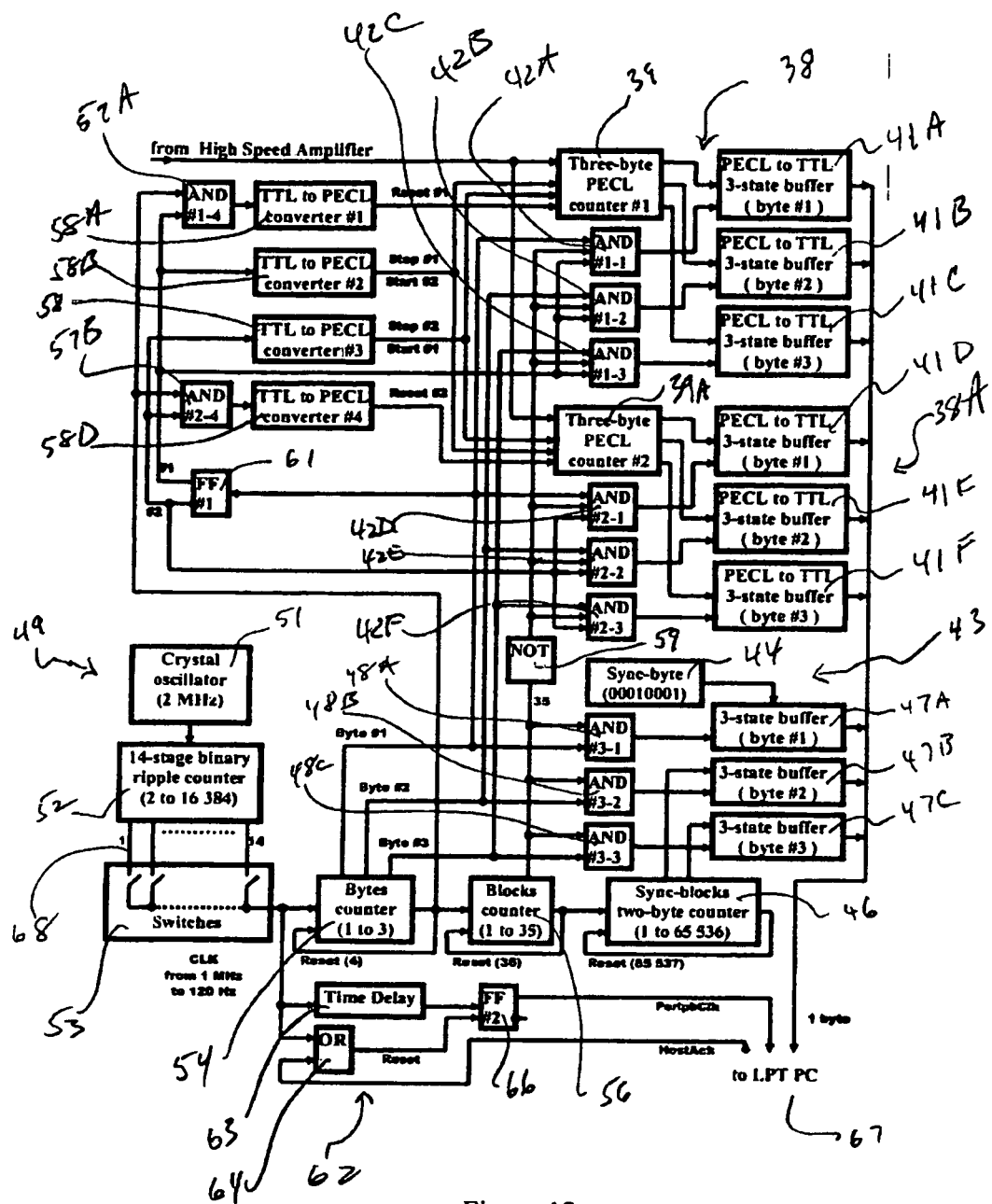
FIG. 12 is a block diagram of a high speed photon counter.

With reference to FIG. 12, a block diagram provides detail of an embodiment of the high speed counter 31 (FIG. 8). In this embodiment the high speed counter comprises a pair of identical counting circuits 38 and 38A. Each counting circuit consists of a three-byte PECL counter 39 and 39A, three PECL to TTL 3-state buffers 41A-C and 41D-F respectively, and three AND gates 42A-C and 42D-F respectively. Each counting circuit is input to a synchronization circuit consisting of a fixed value sync-byte unit 44, a sync-blocks two-byte counter 46, three 3-state buffers 47A-C and 3 AND gates 48A-C.

The high speed counter also contains a control circuit 49 which consists of a crystal oscillator 51, a 14-stage binary ripple counter 52, and a plurality of switches 53 each of which corresponds to a stage of the counter 52. The control circuit 49 also includes a bytes counter 54, the output of which is input to a blocks counter 56. The bytes counter 54 and blocks counter 56 are each connected to the AND gates 42A-F and 48A-C. The output of the bytes counter 54 is also input to a pair of additional AND gates 57A and 57B each of which is connected to one of four TTL to PECL converters 58A-D. A NOT gate 59 is connected to the blocks counter 56 and the AND gates 42A-F and 48A-C. The control circuit contains a flip-Flop connected to each of the four TTL to PECL converters 58A-D. An LPT output control circuit 62 consists of a time delay unit 63, OR gates 64 and a flip-flop.

Pulses from the high speed amplifier 27 are simultaneously provided to the inputs of the 3-byte PECL counters 39 and 39A. One of these counters is always in counting mode, while the other is on hold. Accumulated data is transferred byte after byte to an LPT port 67 through the PECL to TTL 3-state buffer that corresponds to the byte number.

The states of the three-byte PECL counters 39 and 39A are determined by the control circuit signals converted by corresponding TTL to PECL converters 58A-D. As an example, the output signal from the TTL to PECL converter 58B sets and holds the three byte PECL counter 39 in the hold mode and, at the same time, sets the three-byte PECL counter 39A into the counting mode. The output signal from the TTL to PECL converter 58C sets and holds the three byte PECL counter 39A into the hold mode and sets the three-byte PECL counter 39 into the counting mode. The output signals from converters 58A and 58C reset the corresponding three-byte PECL counter after its data has been transferred to the LPT port 67.

After each 102 transmitted bytes three synchro-bytes from the synchronization circuit 43 are initiated. The $1^{st}$ byte has the fixed value of 00010001, as indicated on FIG. 11, and the $2^{nd}$ and $3^{rd}$ bytes represent the then current state of the sync-blocks two-byte counter 46. The synchro-byte output of the counter 46 is passed to the system output 67 through the corresponding 3-state buffers 47A-C.

The crystal oscillator 51 of control circuit 49 generates 2 MHz clock pulses which are passed to the 14-stage binary ripple counter 52. The counter 52 has 14 output pins, indicated generally by reference numeral 68. Each pin outputs clock pulses the initial frequency of which is divided by a coefficient from 2 to 16386. The switches 53 are used to select an appropriate pin from 1-14 and thereby set the clock frequency for the entire circuit. In this embodiment, the switches can set the transmission speed of the data to the LPT port 67 from 122 to 1,000,000 bytes per second.

The clock pulses are passed to the bytes counter 54. After receiving each clock pulse the bytes counter 54 sequentially generates a signal on each of three outputs, indicated as "Byte" numbers 1, 2 and 3 on FIG. 11. Each such signal transmits a corresponding data byte and each data byte is passed to both counting circuits 38 and 38A. Each data signal is also presented to the synchronization circuit 43 via a corresponding AND gate 48A-C.

A high on the $4^{th}$ output from bytes counter 54 resets the counter and is passed to the blocks counter 56 which counts the number of the transmitted 3-byte words. Upon counting the $34^{th}$ 3-byte word, which equals 102 data bytes, the blocks counter 56 generates the signal for the $35^{th}$ 3-byte word. This signal is presented to the AND gates 48A-C which enable the synchronization circuit's data to be presented to the LPT output 67. At the same time, the signal for the $35^{th}$ 3-byte word blocks the output of the counting circuits 38 and 38A. The output signal from blocks counter 56 that corresponds to the $36^{th}$ 3-byte word, resets the counter, as indicated on FIG. 11, and clocks the sync-blocks two byte counter 46 to count the number of 105 byte sequences. The sync-blocks two byte counter 46 resets after a value of 65536 is reached.

Figure 13:
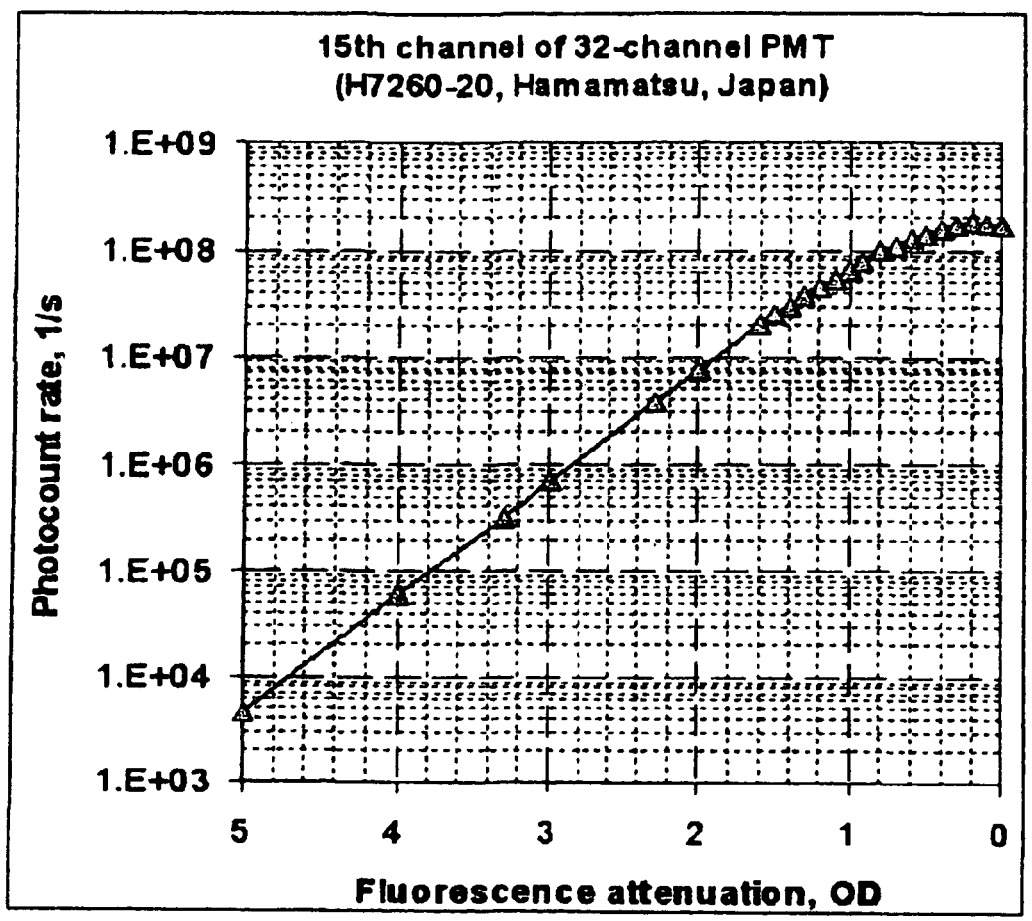
FIG. 13 is a graph showing light vs. photocount characteristics of one channel of a single photon detector.
Figure 14:
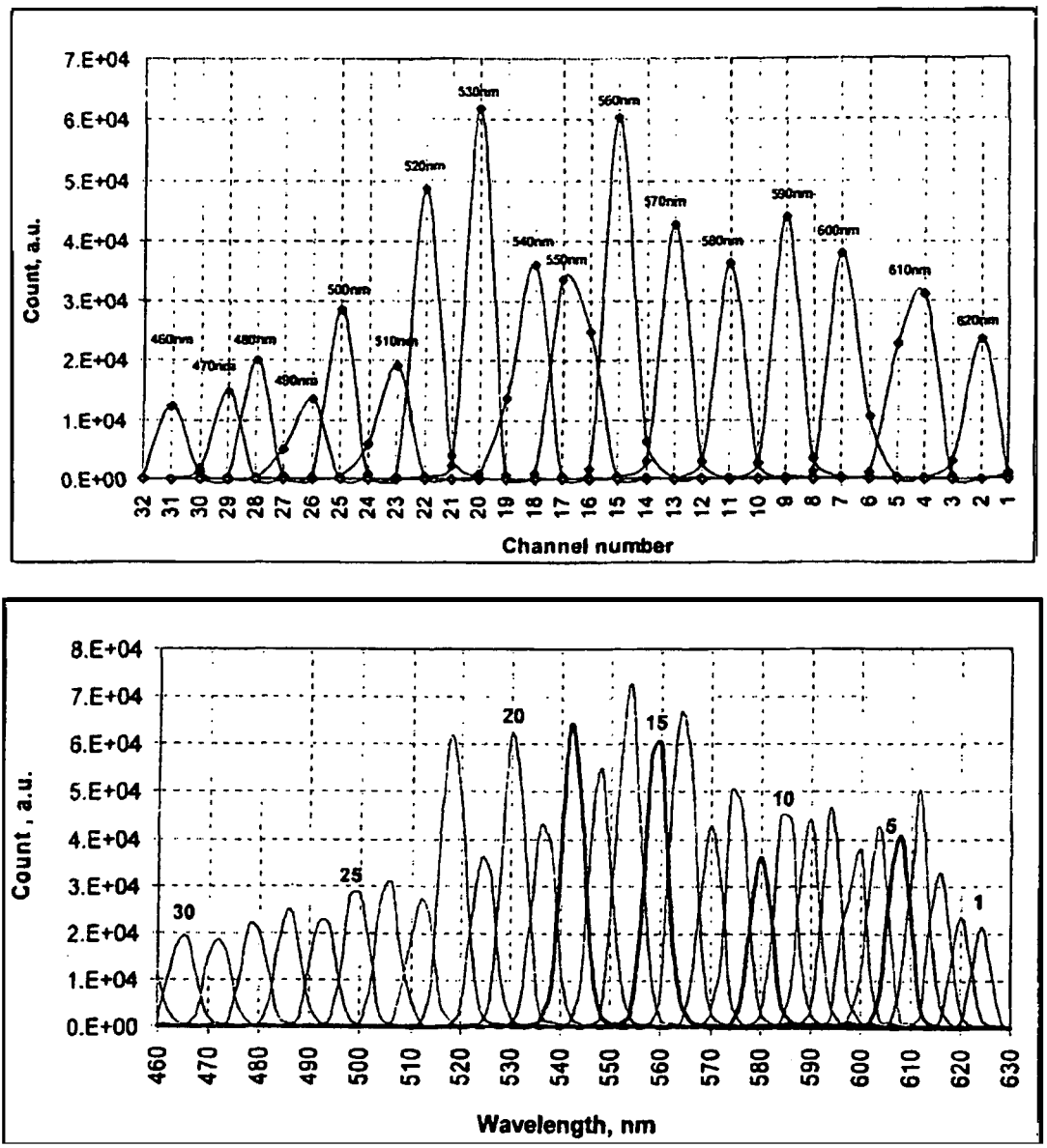
FIG. 14 illustrates channel resolution in the top panel and wavelength resolution in the bottom panel of a spectrometer with a 32 channel PMT sensor.

The flip-flop 61 is triggered by every $1^{st}$ byte pulse from the bytes counter 54. The signals produced by the flip-flop 61 alternately put three-byte PECL counters 39 and 39A into count or hold modes. Such signals also enable or disable the output of the counters and either allows or blocks the transmission of the reset pulse to the counters via AND gates 57A and 57B. FIG. 13 depicts a graph showing the typical light vs. photocount characteristic of one channel of the type of counter depicted in FIG. 12.

Referring again to FIG. 7, typical voltage pulses are depicted at the input and the output of an embodiment of a pulse amplifier. The width of the amplified pulse is approximately 5 ns which is about 5 fold longer than the width of the input pulse. The dynamic range of the detector (the ratio of the maximum photocount to the dark noise) is −20 bit. With the use of data recording software, pulse duration less than 2 ns may be resolved by the counter with pulse amplitude −1.5V.

Due to the sensitivity and linearity of the 32-channel single photon detector of the present embodiment, a photocount rate as high as $5 \times 10^7$ counts per second can be registered. In fact, the linearity of the detector enables an extremely broad range of linear photon counting, for example, up to and exceeding $2 \times 10^7$ photocounts per second. Photon counts as high as $2 \times 10^8$ have also been observed. These count ranges would exceed the detection dynamic range of any known commercial single photon detector. Comparison of the photon detection efficiency of the detector of the present embodiment and an available commercial single photon detector, for example the model SPCM-AQR-12-FC, indicates that at 490 nm the photon detection efficiency of a 32-channel PMT detector of the present embodiment constituted about 20% of the photon detection efficiency of the foregoing commercial SPCM and it decreased to 5% at 610 nm.

With reference to FIGS. 8 and 12, data collected by the counter 31 is transferred to a PC using a standard IEEE 1284 Parallel Port Interface 67. The data is transferred in 105-byte frames using a binary format. Data frames consist of count values obtained for each of the 32 detection channels (3 bytes per channel). Each frame starts with a 6-byte header which includes the following fields: 1-byte counter type, 2-byte frame number, and a 2-byte counting period length measured in milliseconds. The frame number contains the number of the current frame. The number is incremented by 1 for each following frame thus forming a rising sequence with overflow. The frame numbers serve as synchronization marks and are used by the data processing software to find data frames in the continuous data stream. Frame numbers are also used for verification of data integrity and for finding errors introduced by interference in the transmission line. A special software package performs the recording and the on-line visualization of the data transferred by the counter.

In processing fluorescence spectra, the main task of the signal processing is the determination of contributions of individual fluorescent dyes into fluorescent signal generated by dye mixtures composed of n dyes having distinct and known fluorescent spectra. The contributions of individual dyes in the mixture can be found by a decomposition of the fluorescence measured in N independent channels of the spectrometer, provided the spectrometer produces linear response to the detected fluorescence.

By way of example, if the number of the analyzed fluorescent dyes n<N (e.g. <<4 for DNA sequencing) then, using a known system matrix technique $H_{(N \times a)} = (h_1, h_2 \ldots, h_n)$, where $h_i = (h_{1i} \ldots h_{Ni})^T$, $(1 \le i \le n)$ are N-component vectors representing spectra of the fluorescent dyes in the analyzed dye mixture, it is possible to obtain a system matrix H by calibrating the system in advance of the spectral responses for individual fluorescent dyes hi. If $r = (r_1 \ldots r_N)^T$ is the measured fluorescent spectrum of the dye mixture, and $s = (s_1, s_2, \ldots, s_n)^T$ is a vector of component weights representing concentrations of individual fluorescent dyes, then in the presence of noise $\omega = \{\omega_1 \ldots \omega_N\}^T$ the measured spectrum r is:

$$r = Hs + \omega \quad (1)$$

The optimal solution s of Equation (1) depends on the distribution properties of the noise components $\omega_i$. A simplified assumption may be made that $\omega_i$ is independent and, assuming identically distributed normal random values, a well known and computationally efficient minimum variance unbiased solution was achieved by Kay in 1993, (Fundamentals of Statistical Signal Processing. Estimation Theory at p. 97), for estimating ŝ as follows:

$$\hat{s} = (H^T H)^{-1} H^T r \quad (2)$$

In photon counting, individual rate observations $r_i$ have Poisson distribution with equal mean and variance. For higher photocount rates (over 50 counts per observation period), the observed rates are well approximated by superposition of 'true' mean rate $\bar{r}_i$ and Gaussian noise $\omega_i$ with variance depending on the mean rate as follows:

$$r_i = \bar{r}_i + \omega_i, \omega_i \sim N(0, f(\bar{r}_i))$$

More precise solutions can be obtained by g that the components $\omega_i$ independent non-identically distributed normal random variables. The general solution for Equation (1) has been derived heretofore by Kay in 1993, Id, as follows:

$$\hat{s} = (H^T C^{-1} H)^{-1} H^T C^{-1} r \quad (3)$$

where C is the co variance matrix of components $\omega_i$. Due to independence of $\omega_i$ the matrix C is diagonal:

$$C = \begin{pmatrix} \sigma_1^2 & & & 0 \\ & \sigma_2^2 & & \\ & & \ddots & \\ 0 & & & \sigma_N^2 \end{pmatrix} \quad (4)$$

where $\sigma_i^2$ is the variance of $\omega_i$. In practice, the mean rate $\bar{r}_i$ is unknown and the observed rate $r_i$ is used for the computation of the variance:

$$\bar{r}_i \cong r_i.$$

Variances $\sigma_i^2$ are estimated for each measurement. The function that relates $\sigma_i^2$ and $r_i$ is specific for each preprocessing method used to obtain $r_i$. For example, if $r_i$ are obtained directly by counting of photons during a sampling period, then $\sigma_i^2 = r_i$. If background $b_i$ is subtracted from the result of the counting observation, then $\sigma_i^2 = r_i + b_i$. If $r_i$ is obtained by averaging counting observation over k sampling periods, then $\sigma_i^2 = r_i/k$. The estimator of Equation (3) is more accurate, but requires more computational resources than the estimator of Equation (2).

The signal processing technique described above allows background subtraction at the stage of cross-talk removal. This is achieved by creating additional spectrum (column in matrix H) that represents the background. The estimators of Equations (2) and (3) with new matrix H will separate the background from the other spectral components.

Figure 15:
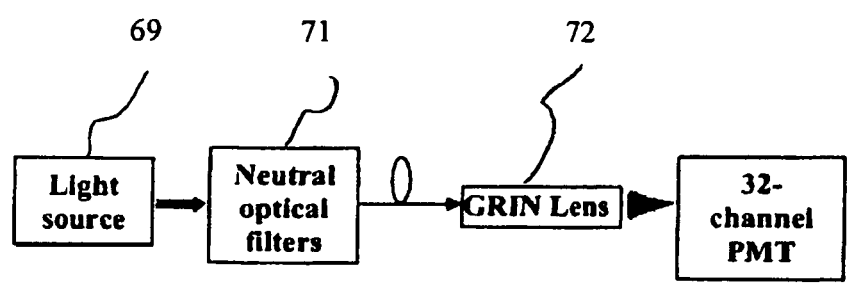
FIG. 15 is a block diagram of an optical system for a single photon detector.
Figure 16:
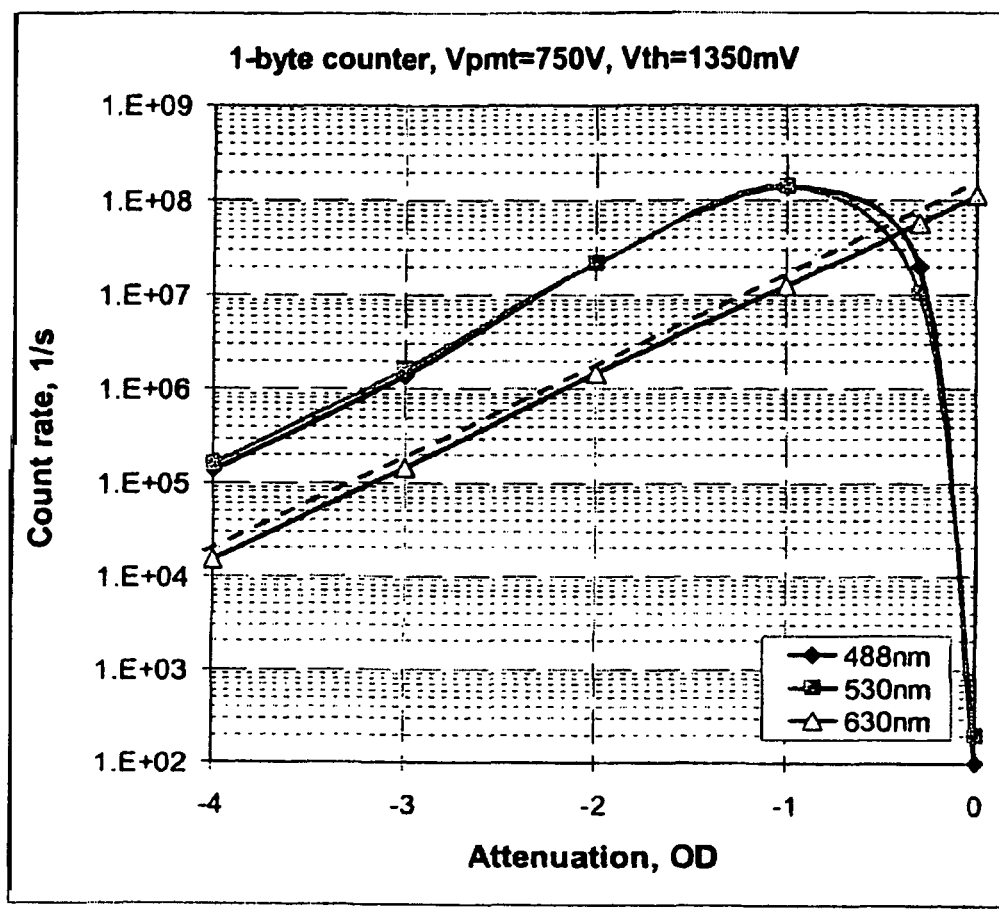
FIG. 16 is a graph showing light vs. photocount characteristics of one channel of the single photon detector of FIG. 15 measured for three wavelengths.

With reference to FIG. 15, there is shown a block-diagram of a measurement setup used for characterization of the single photon detector. In the setup, light from a light source 69, which may be a monochromator or a 532 nm laser, is passed through a set of neutral optical filters 71 and coupled into the fiber terminated with a GRIN lens 72. The light from the GRIN lens is focused onto one of the 32 photocathodes of the 32-channel PMT. Photocount and light characteristics measured for the single photon detector using the setup shown in FIG. 15 with a monochromator as the light source 69 are depicted in FIG. 16. As can be seen, for all three measured wavelengths, the output of the detector remains linear up to 108 photocounts per second and the detector's dynamic range exceeds 2×108 photocounts per second. A significant difference in absolute count rate is illustrated for wavelengths of 4488 nm & 530 nm as compared to 630 nm. There is a decrease of the quantum efficiency of the PMT at wavelengths longer than 600 nm.

Figure 17:
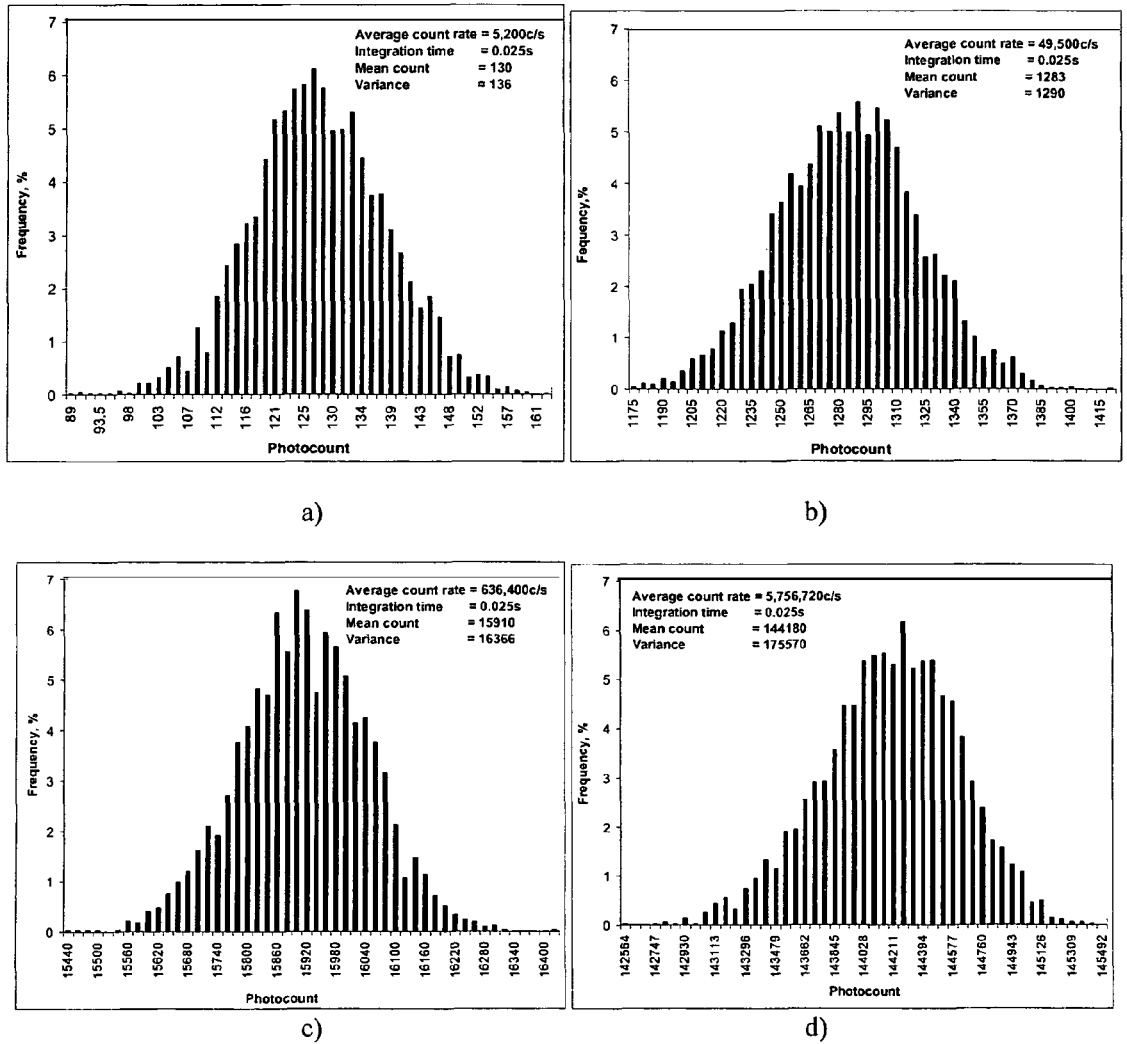
FIG. 17 illustrates histograms of photocount distributions at the output of a photon detection module.

The noise in the photon counting system of the present embodiment is determined by the temporal distribution of photocounts. A correctly operating photon counter utilizes Poisson distribution for which the variance of the photocount rate estimate, e.g., the number of photons counted over the integration period, is equal to its mean value. This sets the lower boundary for the signal-to-noise ratio of the photon detector. FIG. 17 shows the histogram of the photo-count distribution at the output of the photon detection module for four different illumination levels. The photocount was collected during 25 ms intervals and recorded using data recording software for about 30 min for each illumination level. FIG. 17 illustrates a good match between mean values and variances for all four illumination levels. This indicates that the measured noise is only caused by the stochastic nature of the photon fluxes detected by the detector and that the detector itself does not produce any additional noise.

In one embodiment, a single photon spectrometer can be used for applications which require a sensitive detection and recognition of mixtures composed of several known fluorescent dyes. In particular, the spectrometer described herein may be used as a photo-sensor for detection of DNA sequencing which is performed by electrophoresis in a single fused silica capillary using fluorescence excitation with commercially available Ar-ion and Nd-YAG lasers. In order to suppress laser wavelengths 5OD 522 nm and 538 nm laser edge filters (522AELP, 538AELP, Omega Optical Inc, VT, USA) for Ar-ion and Nd-YAG lasers respectively may be used.

Figure 18:
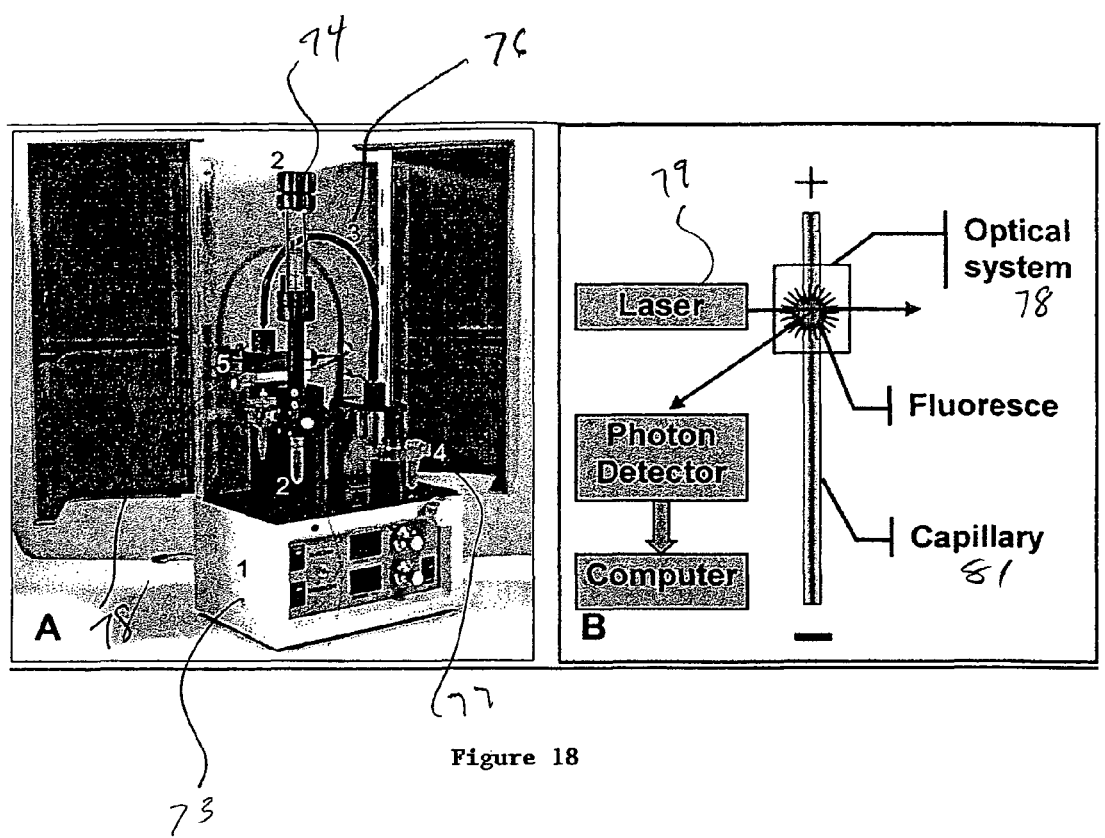
FIG. 18 consists of a photograph and schematic diagram of a single lane DNA sequencer.

With reference to FIG. 18, there is shown a photograph and schematic of an embodiment of a single lane DNA sequencer. DNA samples undergo electrophoretic separation in a single-capillary separation module shown in the photograph. The module consists of a miniature high voltage supply 73 (up to 15 kV) having a built-in voltmeter and ampere meter, a polymer replacement system 74, a temperature control system 76 (25-70° C.±0.01° C.), a tube-changer carousel 77 for DNA samples and running buffer, and a precision optical system 78. With reference to the schematic of FIG. 18, when the fluorescently labeled DNA fragments pass the optical system 78 they are illuminated by a fiberized laser such as, but not limited to, an Ar-ion laser (488 and 514 nm, 20 mW) made by Uniphase, Calif., or an Nd:YAG laser (532 nm, 25 mW, GCL-025-S) made by CrystaLaser, Nev. The laser-induced fluorescence is collected by a fiber 81, which may have a 200 mkm core diameter, and is delivered to the spectral separation module 12 (FIG. 3). In one embodiment, 5OD 522 nm and 538 nm laser edge filters (522AELP, and 538AELP) made by Omega Optical Inc, VT, may be used to suppress laser wavelengths of Ar-ion and Nd-YAG lasers, respectively.

DNA samples labeled with the BigDye Terminator v1.1 sequencing standard obtained from Applied Biosystems (Foster City, Calif.) were denatured in 25 μl Formamide and diluted 1 to 5 in HPLC grade water immediately prior to injection. DNA separation was conducted at 150 V/cm in 40 cm (35 cm separation length) uncoated capillaries, having a 50 μM inner diameter and a 365 μM outer diameter, tilled with POP-7 separation medium at 50° C. In this example, a running buffer was used.

There are at least two effective approaches for estimating fluorescence intensities produced by four dyes used for labeling of A, C, G and T terminators. One such approach is to decompose the measured spectrum according to Equation (3), above. With respect to the decomposition of the entire measured spectrum, the spectral components $c_i$ which describe individual dyes are obtained experimentally by measuring fluorescence emitted by each dye separately and by normalizing the measured vector of photocount rates. The determination of concentrations of individual dyes s[n] in the mixture is performed for each time frame. The obtained sequence of dye concentrations forms four sequencing traces, which are further used for base calling.

Another approach is the application of virtual filters. The method of virtual filters may be used if the component spectra are well separated. Incident light containing spectra with spatially well-separated wavelengths irradiates input ends of fiber bundles having a selected angle of acceptance. Because of the finite angle of acceptance, particular fibers collect signal only from a specific wavelength and deliver signal to a specific channel of the photodetector. As an example, virtual filters may be formed by selecting three PMT channels so that each of three different wavelengths of the fluorescence of each dye is captured by one of the three PMT channels and therefore contributes the most to measurements in the assigned channel and provides a minimum response in the other channels. Such a system renders bandpass filters for detection of multicolor fluorescence unnecessary. In another example, spatially wide spectra of a particular dye and having a particular wavelength are simultaneously captured by a group of several, for example three, fibers or fiber bundles. Such an arrangement allows a significant increase in dynamic range without a decrease in the signal-to-noise ratio of the system.

In one embodiment, a high dynamic range of linearity for spectra with narrow emission spectra may be achieved. There, each of several wavelengths of the fluorescence of each dye is captured by one of the PMT channels and therefore contributes the most to measurements in the assigned channel and provides a minimum response in the other channels. The fibers pass the specific wavelengths to corresponding detectors in a 1×N photodetector. From there, the signals are passed to an M×N photodetector for collecting spatially separated spectra. Projection optics may be used to project the $N_{th}$ wavelength on the $N_{th}$ column of the M×N photodetector. Therefore, signals of particular wavelengths are simultaneously collected by M single photon photodetectors. This arrangement also achieves a high dynamic range of linearity and a high signal-to-noise ratio for the system.

In the data processing approaches for the described embodiments, the four sequencing traces undergo standard processing which includes noise filtering or smoothing, baseline subtraction, crosstalk removal, mobility shift correction, peak height and spacing equalization. After re-sampling to 7-15 points per peak the traces are stored in SCF format and processed by standard base calling PHRED software. The result of the processing is returned as a sequence of base-calls with their positions and quality scores.

Figure 19:
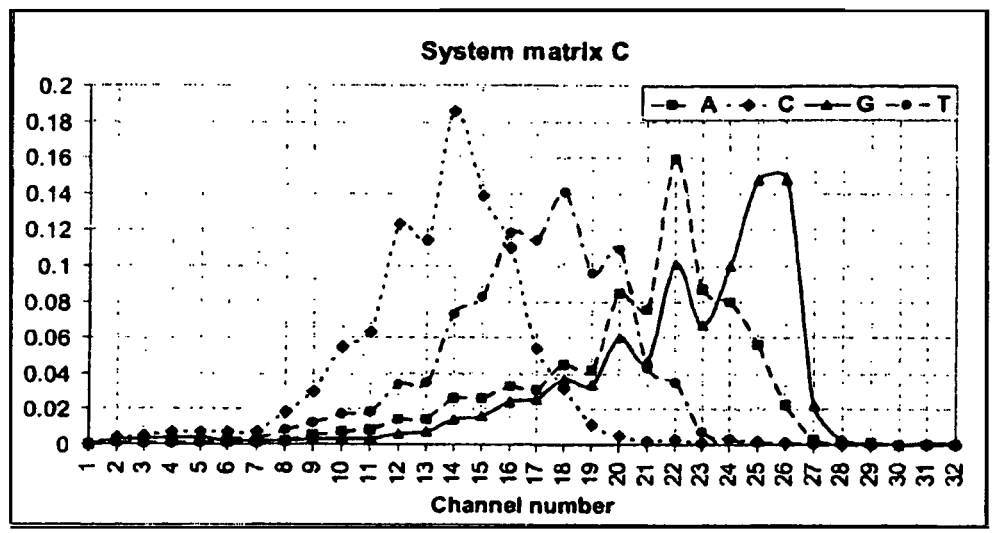
FIG. 19 consists of a graph showing the system matrix C in the top panel and color deconvolution matrices in the bottom panel used for processing DNA sequencing data.

As indicated above, there are at least two approaches to processing of the DNA sequencing data. With reference to FIG. 19, which illustrates a system matrix graph 82 and color deconvolution matrices 83 and 84 for Ar-ion and Nd-YAG lasers respectively, a simplified data processing approach would use signals obtained from channel 18 (546 nm), channel 15 (568 nm), channel 11 (589 nm) and channel 5 (610 nm) of the PMT. Channels 18, 15, 11 and 5 correspond respectively to G, A, T and C. The derived color deconvolution matrices 83 and 84 for Ar-ion and Nd-YAG lasers are illustrated in spread sheet format in the lower panel of FIG. 19. In contrast, spectral components $h_i$ for determination of the system's matrix H may be obtained experimentally by measuring fluorescence emitted by each dye separately and by normalizing the measured vector of photocount rates shown in the upper panel graph 82 of FIG. 19.

The foregoing approaches to processing of the sequencing data yield similar sequencing traces and base calling quality. However, for measurements characterized by small signal-to-noise ratios the decomposition of entire measurement spectrum gives better results since it uses the entire information about the fluorescence emitted by each dye rather than just the fluorescence obtained in only four selected channels of the spectrometer. Another advantage of using the entire fluorescence spectrum obtained from the dye is a significant increase of the detection dynamic range. Indeed, in the 32-channel photosensor described herein the channels have linear response up to $2 \times 10^7$ photocounts per second and if the measured fluorescent dye has a broad spectrum, the linear range of the detection for this dye will be proportional to the number of simultaneously illuminated channels of the sensor.

Figure 20:
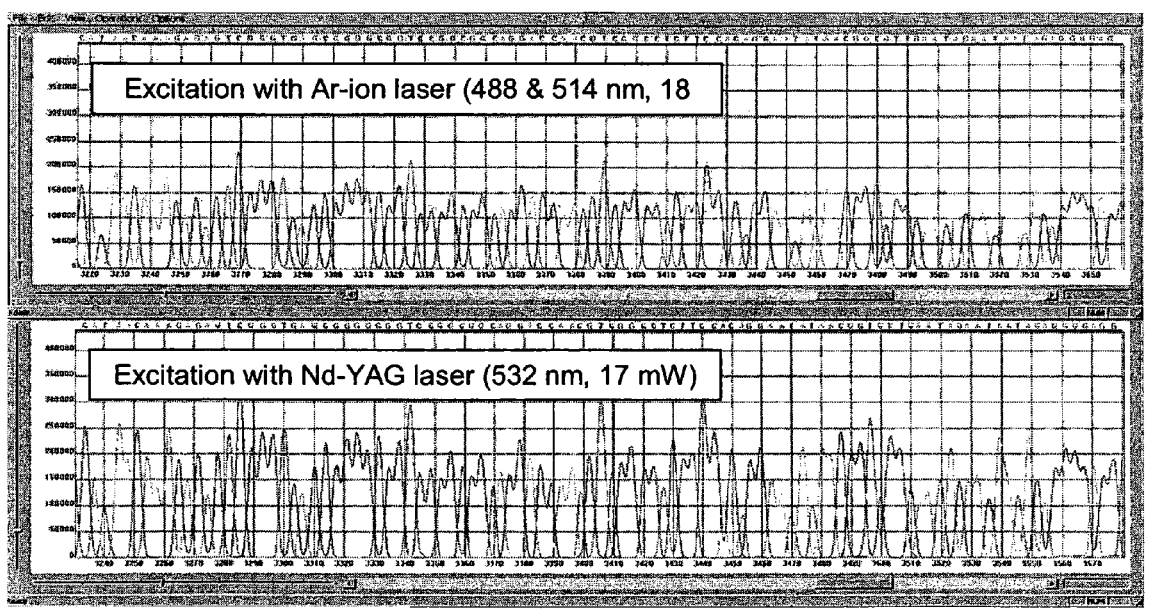
FIG. 20 are graphs of DNA sequencing traces and base calling quality scores.

FIG. 20 illustrates two DNA sequencing traces and base calling quality scores obtained with an embodiment of the spectrometer described herein using the Ar-ion and Nd-YAG lasers. The sequencing traces recorded with the two lasers look very similar and the quality scores are nearly identical. The obtained Q20 sequence read length is as long as about 650 base pairs which is in a very good agreement with the read lengths obtained for the same capillary length in commercial DNA sequencers, such as model ABI-3730 from Applied Biosystems Inc.

Figure 21:
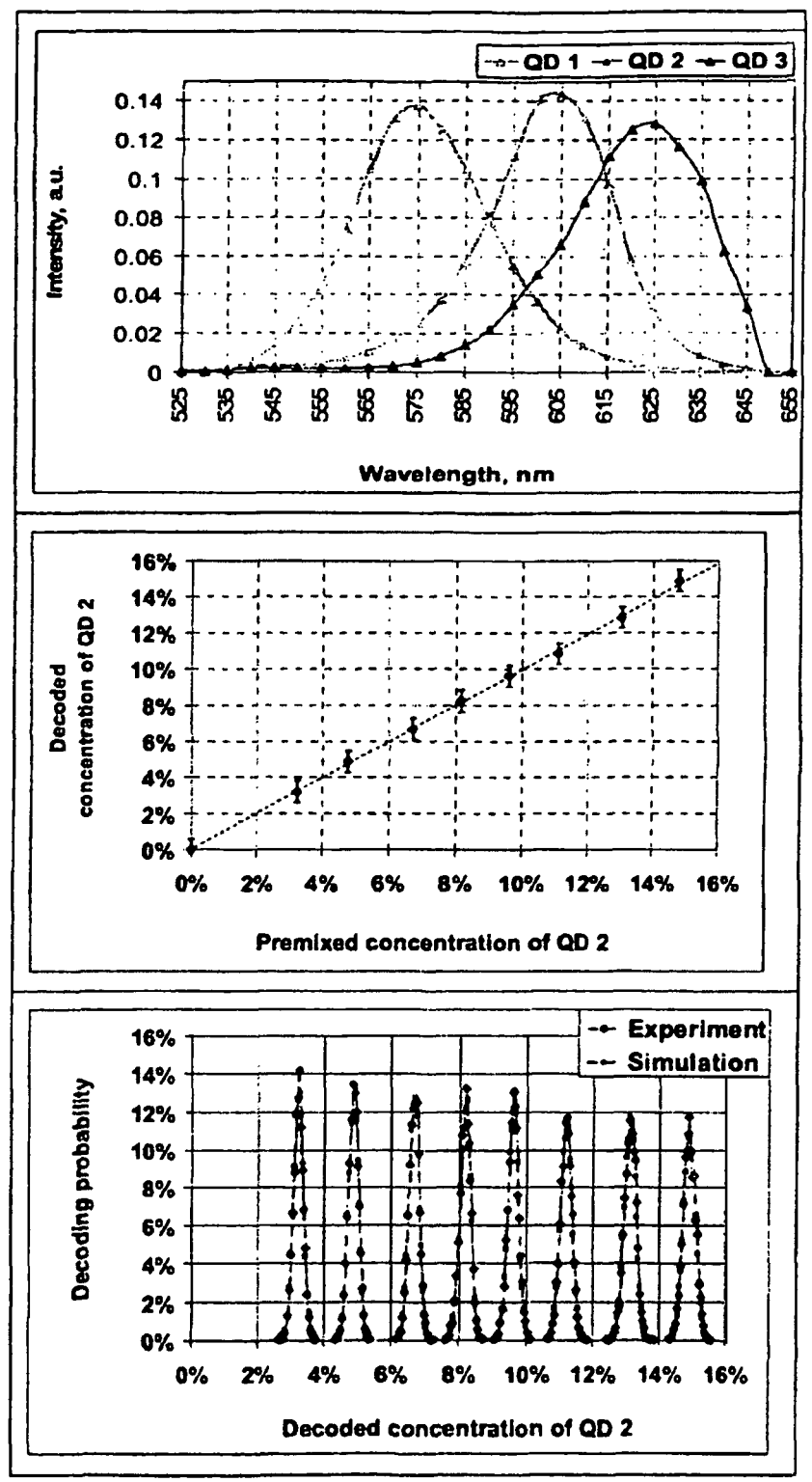
FIG. 21 consists of graphs showing recognition of color codes and accuracy of computer simulated color decoding.

In one embodiment, the single photon spectrometer may recognize and accurately decode color codes. With reference to FIG. 21, the upper panel illustrates measurements and decoding of mixtures containing three types of QDs with strongly overlapping spectra. The middle panel of FIG. 21 illustrates that when the content mixture of QD2 is varied from 0% to 15% a nearly perfect match of the premixed and decoded concentrations can be achieved. Curves on the bottom panel of FIG. 21 illustrate the decoding statistics obtained by performing several thousand measurements for each QDs mixture (about 10,000 photons per measurement) as well as the decoding results obtained for computer simulation of the measurements performed by the single photon spectrometer.

Figure 22:
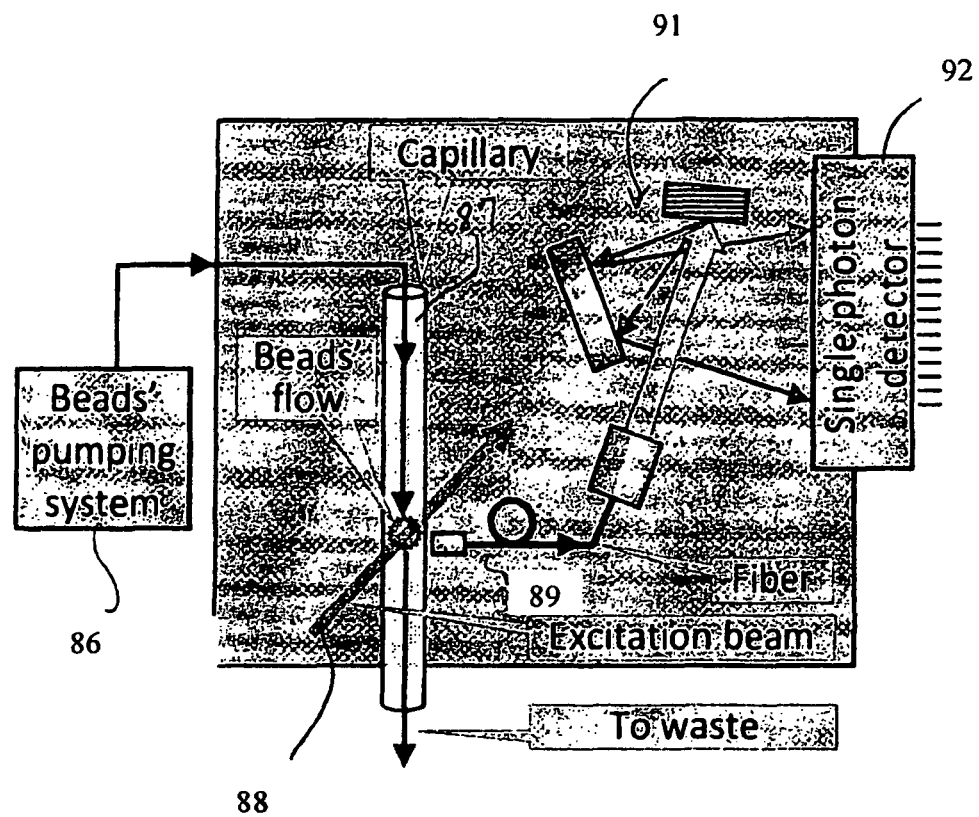
FIG. 22 is a schematic drawing of a bead detection system.

In one embodiment the single photon spectrometer may detect color-encoded microparticles. With reference to FIG. 22, there is illustrated a bead reader system in which individual beads are suspended in a buffer fluid held in a beads' pumping system 86. The beads are measured by pushing them through a capillary 87 at a high speed. An excitation beam 88 excites fluorescence in the beads. The fluorescence is detected by an optical fiberized detector 89 and is presented through a suitable spectrometer or optical reflection system 91 to a single photon detector 92. The detected signals are recorded by a computer (not shown) and the recorded data is suitably processed. In one embodiment, the pumping system 86 is a programmable micro-pump and the capillary 87 is a 25 µm ID capillary. The capillary is inserted into an optical head (not shown) to ensure a uniform illumination of the capillary by the excitation beam 88. The beam 88 is produced by a suitable fiberized laser source (not shown). When the beads pass through the laser beam, they emit fluorescence which is collected by the fiberized micro-objective 89. The collected fluorescence is delivered to the spectrometer 91, where it is detected by the single photon detector 92 which, in this embodiment, is a high speed multi-channel detector.

Figure 23:
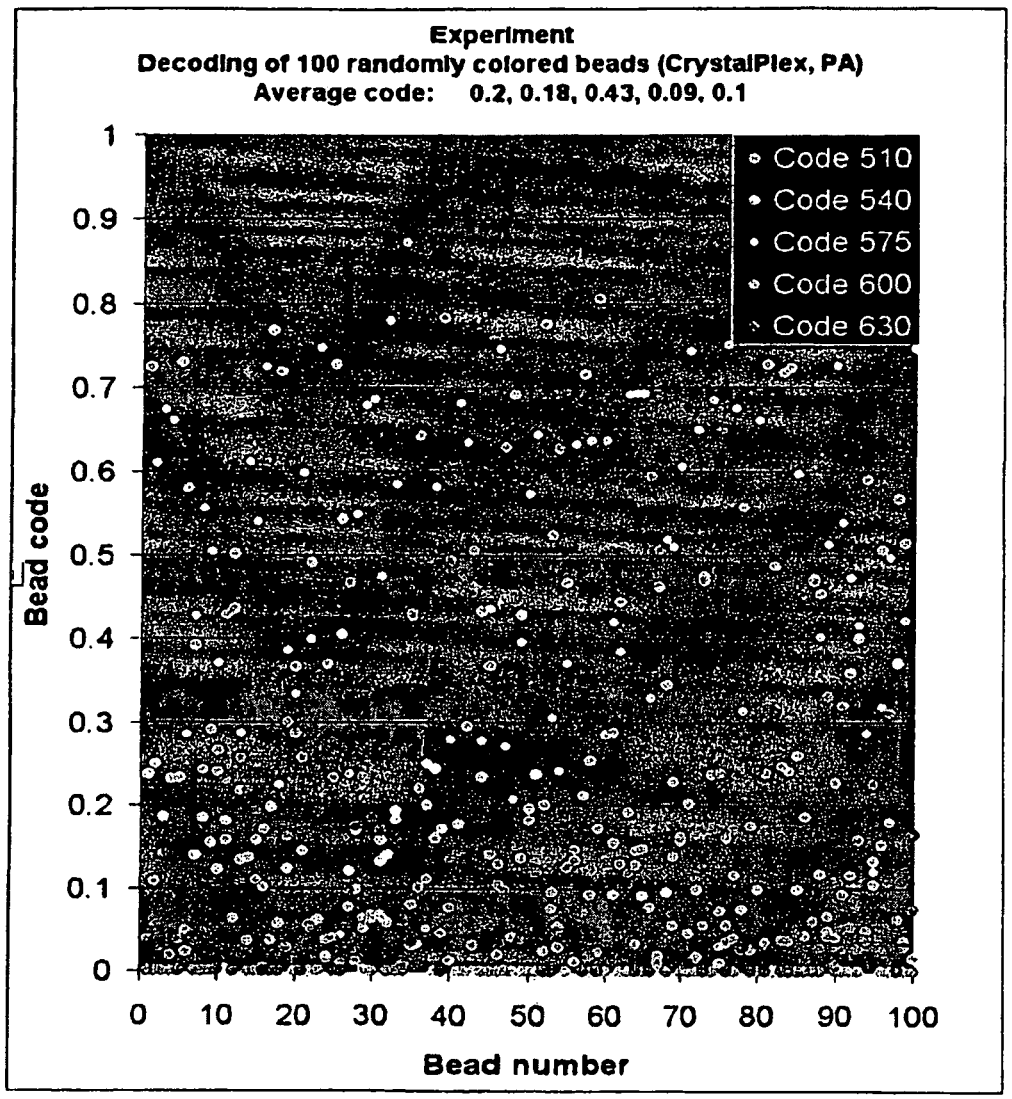
FIG. 23 is a graph showing recognition of randomly colored beads.

With reference to FIG. 23, the bead reader of FIG. 22 may be used to carry out measurements of randomly colored beads. In one embodiment, measurements were made of polystyrene beads colored with quantum dots. The results of decoding obtained for 100 such beads are illustrated in FIG. 23, where the x axis shows the bead number in the order detected by the bead reader and the y axis shows the bead codes normalized to 1.

Figure 24:
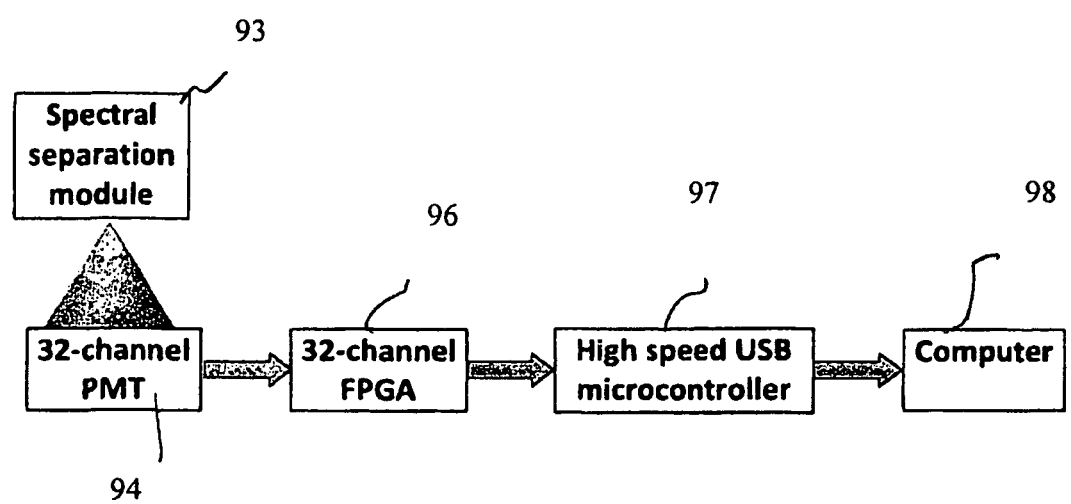
FIG. 24 is a block diagram of a 32 channel fast, large dynamic range single photon spectrometer.
Figure 25:
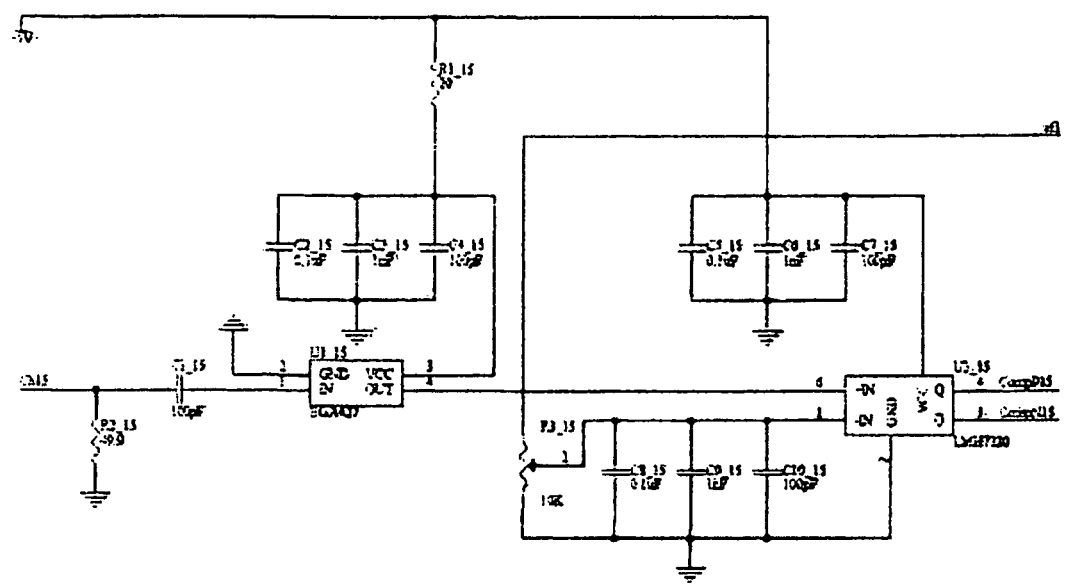
FIG. 25 is a schematic circuit diagram for a 32 channel pulse amplifier.

The main characteristic of the foregoing beads' detection system is the number of beads that can be detected per unit time and decoded with the required accuracy. In general, decoding accuracy is determined by the number of photons collected during the bead's detection time. It will be understood that for commercially available sets of quantum dots, decoding accuracy as high as 99 percent can be obtained if the total number of photons collected from the bead will be larger than $10^4$. The rate at which detection of the beads occurs depends on the dynamic range of the photon detector. With reference to the block diagram of FIG. 24, in one embodiment a beads' detection rate as high as $10^4$ per second is obtained with a photon detector consisting of a spectral separation module 93, a 32 channel PMT 94, a 32 channel FPGA 96, a high speed USB microcontroller 97 and a computer 98. Such a system has a linearity range of $10^8$ photocounts per second per channel, and a data transfer rate of 32 MB per second. A schematic circuit diagram of one channel of a 32 channel pulse amplifier of the system shown in block diagram in FIG. 24 is illustrated in FIG. 25.

Although various embodiments have been described above with a certain degree of particularity or precision, or with reference to one or more individual embodiments, those skilled in the art could make numerous alterations to the disclosed embodiments without departing from the spirit or scope of the invention as claimed herein. It is intended that all of the subject matter contained in the above description and shown in the accompanying drawings shall be interpreted as illustrative only of particular embodiments and not limiting. Changes in detail or structure may be made without departing from the elements of the invention as defined in the following claims.

What is claimed is:

1. A single photon sensor comprising:
At least one multichannel photosensor including a linear photo multiplying tube array selected from the group consisting of linear photo multiplying tube arrays having more than 4 photosensor channels, more than 8 photosensor channels, more than 16 photosensor channels and more than 32 photosensor channels, each photosensor channel having photosensitive pixels adapted to receive distinct light spectra from a light spectra separator to which optical fibers communicate polychromatic light, and producing current pulses in response to single photons of said received light spectra;
A multichannel amplifier, each amplifier channel adapted to receive said current pulses corresponding to light spectra from a corresponding one of said sensor channels of said multichannel photosensor and to amplify said current pulses; and
A multichannel photon counter, each counter channel adapted to receive said amplified current pulses from a corresponding one of said amplifier channels of said multichannel amplifier, said multichannel photon counter having an integrator adapted to sum said amplified current pulses in each counter channel over a predetermined time interval.

2. The single photon sensor of claim 1 in which said linear photo multiplying tube array contains 32 channels.

3. The single photon sensor of claim 2 in which said multichannel amplifier comprises 32 pulse amplifying channels, each of said pulse amplifying channels being adapted to receive said current pulses from a corresponding one of the 32 channels of said linear photo multiplying tube array.

4. The single photon sensor of claim 1 in which each of said current pulses produced by each channel of said at least one multichannel photosensor has a duration $\tau_{PULSE}$ less than 2 nanoseconds.

5. The single photon sensor of claim 1 in which each of said current pulses produced by each channel of said at least one multichannel photosensor has a duration $\tau_{PULSE}$ less than 1 nanosecond.

6. The single photon sensor of claim 1 in which each of said current pulses produced by each channel of said at least one multichannel photosensor has a duration $\tau_{PULSE}$ less than 0.1 nanoseconds.

7. The single photon sensor of claim 1 in which each of said current pulses produced by each channel of said at least one multichannel photosensor has a duration $\tau_{PULSE}$ less than 0.01 nanoseconds.

8. The single photon sensor of claim 1 in which the range of linear photon counting of said multichannel photon counter is at least $10^7$ photocounts per second.

9. The single photon sensor of claim 1 in which the range of linear photon counting of said multichannel photon counter is $10^8$ photocounts per second.

10. The single photon sensor of claim 1 in which a range R of linear photon counting of said multichannel photon counter is $R \geq 1/\tau_{RESPONSE}$ where $\tau_{RESPONSE}$ is the time required by said single photon counter to respond to a single photon.

11. The single photon sensor of claim 1 in which said multichannel photosensor comprises a silicon photomultiplier, each of the channels of which comprises a matrix of individual pixels, said channels being connected together in parallel on a common silicon substrate.

12. The single photon sensor of claim 1 comprising a pair of said multichannel photosensors and a light beam splitter adapted to receive incident polychromatic light and to produce a beam of polychromatic light for each multichannel photosensor, each of said beams of light being incident upon a light spectra separator.

13. The single photon sensor of claim 12 in which each sensor channel of each of said pair of multichannel photosensors has photosensitive pixels adapted to receive distinct light spectra from a light spectra separator and to produce current pulses in response thereto.

14. The single photon sensor of claim 12 in which said light beam splitter comprises a dichroic mirror.

15. The single photon sensor of claim 12 in which said light beam splitter comprises a semitransparent mirror.

16. The single photon sensor of claim 1 in which said polychromatic light consists of fluorescent spectra produced by a mixture formed by a plurality of fluorescent dyes.

* * * * *

UNITED STATES PATENT AND TRADEMARK OFFICE
CERTIFICATE OF CORRECTION

PATENT NO. : 8,582,098 B2  
APPLICATION NO. : 12/734365  
DATED : November 12, 2013  
INVENTOR(S) : Tsupryk et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 684 days.

Signed and Sealed this
Twenty-second Day of September, 2015

Michelle K. Lee
*Director of the United States Patent and Trademark Office*